US011425889B2

(12) United States Patent
Koronyo et al.

(10) Patent No.: US 11,425,889 B2
(45) Date of Patent: Aug. 30, 2022

(54) VISUAL STIMULI MAZE TEST FOR DETECTING VISUAL ABNORMALITIES IN PRODROMAL ALZHEIMER'S DISEASE AND IN ALZHEIMER'S DISEASE

(71) Applicant: Cedars-Sinai Medical Center, Los Angeles, CA (US)

(72) Inventors: Maya Koronyo, Los Angeles, CA (US); Yosef Koronyo, Los Angeles, CA (US); Keith L. Black, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 492 days.

(21) Appl. No.: 16/301,585

(22) PCT Filed: Jun. 2, 2017

(86) PCT No.: PCT/US2017/035835
§ 371 (c)(1),
(2) Date: Nov. 14, 2018

(87) PCT Pub. No.: WO2017/210645
PCT Pub. Date: Dec. 7, 2017

(65) Prior Publication Data
US 2019/0117145 A1 Apr. 25, 2019

Related U.S. Application Data

(60) Provisional application No. 62/344,877, filed on Jun. 2, 2016.

(51) Int. Cl.
*A01K 15/02* (2006.01)
*A01K 1/03* (2006.01)
(Continued)

(52) U.S. Cl.
CPC .............. *A01K 15/02* (2013.01); *A01K 1/031* (2013.01); *A01K 2267/0312* (2013.01);
(Continued)

(58) Field of Classification Search
CPC ................................ A01K 1/031; A01K 15/02
See application file for complete search history.

(56) References Cited

U.S. PATENT DOCUMENTS 3,857,364 A 12/1974 Miller, Jr.
2003/0024482 A1 2/2003 Gondhalekar et al.
(Continued)

FOREIGN PATENT DOCUMENTS

CN 102440197 A 5/2012

*Primary Examiner* — Jessica B Wong
(74) *Attorney, Agent, or Firm* — Nixon Peabody LLP

(57) ABSTRACT

Disclosed herein is a rodent and human behavioral test for evaluating visual dysfunctions associated with the retinal changes in Alzheimer disease progression. In one example, the inventors developed a maze that tests rodent's ability to identify (1) specific contrasts, (2) specific colors, (3) certain items in the visual field, and (4) other 'non-typical' peripheral and night vision functions associated with AD. For instance, the inventors developed a maze the tests the rodents ability to avoid certain colors or contrasts gradients. The maze may include certain rooms with specific visual markers (e.g., colors, contrasts, objects or other visual features) that also contain shock plates.

15 Claims, 19 Drawing Sheets

(51) Int. Cl.
   *A61B 3/00* (2006.01)
   *A61B 3/02* (2006.01)
   *A61B 3/06* (2006.01)
   *A61B 5/00* (2006.01)

(52) U.S. Cl.
   CPC ............ *A61B 3/0091* (2013.01); *A61B 3/022* (2013.01); *A61B 3/06* (2013.01); *A61B 5/4088* (2013.01); *A61B 2503/40* (2013.01)

(56) References Cited

U.S. PATENT DOCUMENTS

| | | | |
|---|---|---|---|
| 2011/0094453 A1 | 4/2011 | Burwell | |
| 2014/0167958 A1* | 6/2014 | Kimchi | A01K 29/005 340/539.13 |
| 2016/0270364 A1* | 9/2016 | Woolf | A61B 5/1105 |
| 2017/0308755 A1* | 10/2017 | Ala-laurila | G06K 9/00744 |

* cited by examiner

Follow up study on the visual stimuli test plus maze in ADtg mice. Using diverse wavelengths and intensities in the inferior visual field in a custom-made plus maze reveals peripheral visual deficits in ADtg mice

| Mice Strain | Light intensity | Percent of time spent in each arm | | | |
|---|---|---|---|---|---|
| | | Reverse dark-light cycle | | | |
| | | White | Red | Blue | Green |
| APP/PS1 transgenic | High | 9.44 | 16.50 | 7.78 | 27.16 |
| | Mid | 11.00 | 30.48 | 15.00 | 7.62 |
| | Low | 2.82 | 40.07 | 7.20 | 13.71 |
| WT counterpart | High | 22.51 | 32.53 | 10.81 | 14.99 |
| | Mid | 25.04 | 29.31 | 13.97 | 17.50 |
| | Low | 5.32 | 34.89 | 25.86 | 21.03 |

FIG. 19

VISUAL STIMULI MAZE TEST FOR DETECTING VISUAL ABNORMALITIES IN PRODROMAL ALZHEIMER'S DISEASE AND IN ALZHEIMER'S DISEASE

CROSS-REFERENCE TO RELATED APPLICATIONS

This application is a National Phase of International Application No. PCT/US2017/035835 filed June 2, 2017, currently pending, which designated the U.S. and that International Application was published under PCT Article 21(2) in English, which also includes a claim of priority under 35 U.S.C. § 119(e) to U.S. provisional patent application No. 62/344,877 filed Jun. 2, 2016, now expired, the entirety of which is hereby incorporated by reference.

FIELD OF THE DISCLOSURE

The present invention is directed to mazes for testing visual function. More particularly, the present disclosure relates to a device, a method, and a system for behavioral test for evaluating visual dysfunctions associated with the retinal changes in Alzheimer disease progression.

BACKGROUND OF THE DISCLOSURE

The following description includes information that may be useful in understanding the present invention. It is not an admission that any of the information provided herein is prior art or relevant to the presently claimed invention, or that any publication specifically or implicitly referenced is prior art.

There is very limited early ability to diagnose and monitor Alzheimer's disease (AD). AD is the most common cause of senile dementia in the United States and Europe. Currently, there are no effective treatments or feasible screening tools for early detection and monitoring progression of AD.

Given the disease's prevalence and poor prognosis, the development of animal models has been a high research priority. Transgenic modeling has been pursued on the basis of the amyloid hypothesis and has taken advantage of mutations in the amyloid precursor protein (APP) and the presenilins (PS) that cause familial forms of Alzheimer's disease. Current evidence indicates that amyloid-related changes likely occur 10-20 years prior to symptom manifestations, suggesting that they may be excellent biomarkers for prodromal AD if adequate detection methods can be implemented.

There is an unmet need for a noninvasive detection of early signs of AD with high specificity and sensitivity to facilitate screening of at-risk individuals, allowing for earlier and more effective intervention.

SUMMARY OF THE DISCLOSURE

Definite Alzheimer's disease (AD) diagnosis at early stages is vital for targeting intervention, yet such diagnosis is currently unavailable. Noninvasive detection of the pathological hallmark, amyloid-ß protein (Aß) plaques, is limited in the brain. However, patients with AD also develop Aß plaques in the retina, possibly at presymptomatic stages. Accordingly, the Aß plaques in the retina may provide a superior alternative target for early testing.

Impairments have been documented as some of the earliest symptoms occurring in patients with AD. In particular, impairments in visual field, contrast sensitivity and color vision were consistently reported in AD patients. However, no visual test currently exists to detect those functional changes. Accordingly, the inventors investigated the development of the Aβ plaques, and discovered that they often occur in distinct geographical regions in the Alzheimer's disease (AD) retina. Therefore, the inventors determined that a visual test that detects visual dysfunction associated with the areas of the retina affected in AD may reliably screen for AD.

A number of visual test exist for rodent models, however, all of them test visual acuity and other visual dysfunctions related to retinal areas that are not typically affected in Alzheimer's disease. Therefore existing visual tests for rodent models would detect any visual functional changes in AD transgenic models, and would not be limited to the visual abnormalities caused by AD. As such, existing tests would capture many false positives and would not provide a reliable screening model.

Accordingly, the present invention discloses a highly sensitive visual test to detect mild and specific changes in the vision of rodent models of AD. These changes could be then associated with the appearance of amyloid-beta plaques in the retina and can provide an earlier indication for functional impairment prior to manifestation of cognitive decline.

Furthermore, harnessing a human body's own immune system to fight various types of dysfunctions, including AD, is a powerful approach. The presently disclosed device, method, and system for early detection of AD would allow further study of immunological mechanisms of repair and regeneration in the central nervous system in transgenic rodent models in an attempt to identify targets for effective immune-modulation therapies. A well-controlled adaptive and innate immune responses can limit neurotoxicity, reduce neuroinflammation, enhance neuroprotection, restore brain homeostasis, preserve synapses, and retain cognitive function.

In some examples of the present disclosure, a rodent behavioral test for evaluating visual dysfunctions associated with the retinal changes in AD models is disclosed, including, but not limited to: (1) visual field, (2) contrast and color distinction, and (3) other 'non-typical' peripheral and night vision functions. These tests can be applied in AD rodent models, including, for example, APP/PS 1 transgenic mice (modeling Alzheimer's disease) compared to their wild-type counterparts (e.g. C57bl/6 strain). Accordingly, this visual test may be useful in diagnosis and monitoring the progression of the early stages of AD in a rodent model.

Visual Plus Maze Device and Test

In one example of the present disclosure, a maze that tests rodent's ability to identify (1) specific contrasts, (2) specific colors, (3) certain items in the visual field, and (4) other 'non-typical' peripheral and night vision functions associated with AD is disclosed. For instance, the maze may test the rodents ability to avoid certain colors or contrasts gradients. The maze may include certain rooms with specific visual markers (e.g., colors, contrasts, objects or other visual features) that also contain shock plates.

Accordingly, if the rodent's visual function is normal, the rodent could learn which rooms, halls, or areas with certain visual markers are associated with the negative shock stimulus and avoid those rooms. Otherwise, if the rodent's visual function is impaired, and the visual markers cannot be identified, the rodent would re-enter rooms with visual markers known to be associated with shock anyway, and receive the shock stimulus. Accordingly, if the visual markers are designed to test retinal dysfunctions associated with AD, the inability of the rodent to distinguish the visual markers and entering rooms with shock associated visual markers would indicate that rodent has developed retinal plaques associated with AD or that could be associated with AD.

Distinct Rodent Container Rooms/Passages

The rodent maze or container for performing the test may be any suitable container for rodents that contain visually distinct areas or rooms the rodent has the option to enter. Additionally, the container connections, pockets or compartments for visual markers to be attached or connected. In some examples, the rodent container may include four separate hallways, wings or rooms, that are linked in the center to form a cross patterns (from overhead). Accordingly, in this configuration, the rodent may be placed in the center, and then the rodent has the choice of entering four different rooms. The hallways may be at any suitable angles, but in one example may be 90 degrees to provide visual distinct choices where the rodent can see down the entire room by standing in the center of the cross.

In some examples, the maze may contain only three rooms or hallways, the angle between each room ideally being equal (e.g., 120 degrees) so that biases or other differences are not associated with certain passage choices. Additionally, in other examples, the maze may be one long hallway, with two rooms or areas on either side of a center portion. In that example, the rodent could be placed in the center of the long hall and the rodent would have two choices—of rooms in which to enter.

These maze configurations allow the rodent to see each of the alternatives if it stands at one spot when first placed inside the maze. Accordingly, other options may be utilized that only present the rodent with one color at a time—for instance a larger maze with long passage ways with a section of the passage way lit (e.g., do not cross area) with shock places in that area of the passage. Therefore, different configurations may be designed that associate the shock plate or other negative stimulus with certain visual markers.

The maze may be made of PLEXIGLAS or other transparent material so that visual markers may be placed outside of or behind the maze walls. In other examples, the maze may be constructed from any suitable material and the visual markers may be placed on the inside of the walls.

Visual Markers

The visual markers may include any variety of markers attached to specific rooms, hallways or areas of a rodent container or maze. For instance, the visual markers may be colored lights (e.g., LEDs), colored inserts, or other objects. Visual markers may be placed in certain areas, rooms, or walls of the maze.

In some examples, visual markers may be a string of lights that can each change a different color or shade of a color. Accordingly, a string of lights, which each showing a slightly darker/lighter shade of the same color can provide a useful tool for easily generating different contrasts. In other examples, inserts that have a gradient of color may also be utilized. In some examples, a first insert with a first color may be inserted behind a first wall, and then a second insert with a color that is different from the first color may be placed behind an adjacent wall or walls.

Negative Stimulus

Negative stimulus may include, e.g., a shock (plates), odor, capsaicin, loud noise, or other negative stimulus. Accordingly, in some examples, the shock stimulus may be delivered using metal plates in the floor of the maze. In some examples, a capsaicin mist or loud noise may be triggered by a mouse entering a certain hallway or area of the hallway associated with or in physical proximity to a certain visual marker.

In one example, the inventors developed a maze consists of four arms (45 cm long) extending from a central arena (10×10 cm). The arms were angled at 90° to each other, yielding a plus shape. All four arms of the maze (45×10 cm) had black sidewalls (15 cm high). The maze was elevated on a tripod 70 cm above the floor. A different LED array of lights (Blue, Red, Green, White) was positioned on the floors of each arm near the arm's end. Each LED included a dimmer, which enabled intensity optimization.

Using this example maze, a test at various light intensities was carried out. Light intensities were measured using a light meter (Zico-Zi-7811) two centimeters from the edge of the arm at the same height as the mouse is positioned. In addition changing floor color platform and triangular platforms are creating different inferior field contrasts.

EMBODIMENTS

Embodiment 1

A maze for evaluating a rodent, the maze comprising:
a first room;
a second room, wherein the first and second room comprise floors and walls configured to allow a rodent to traverse between the rooms;
a negative stimulus deliverer in the first room;
a first visual marker in the first room and a second visual marker in the second room, wherein the first visual marker is different than the second visual marker; and
a control system to power the negative stimulus deliverer.

Embodiment 2

The maze of embodiment 1, wherein the first and second visual markers are light sources.

Embodiment 3

The maze of embodiment 2, wherein the first and second visual markers are LEDs.

Embodiment 4

The maze of embodiment 1, wherein the first and second visual markers are opaque plates.

Embodiment 5

The maze of embodiment 1, wherein the first and second visual markers are objects.

Embodiment 6

The maze of embodiment 5, wherein the first and second visual markers are stairs.

Embodiment 7

The maze of embodiment 1, wherein the first and second visual markers comprise at least two different hues of the same color, and where the first visual marker has a higher or lower contrast difference than the second visual marker.

Embodiment 8

The maze of embodiment 1, wherein the first and second visual markers comprise at least two different colors.

Embodiment 9

The maze of embodiment 1, wherein the negative stimulus deliverer is a shock plate or prongs.

Embodiment 10

The maze of embodiment 1, wherein the negative stimulus deliverer is a capsaicin spray.

Embodiment 11

The maze of embodiment 1, wherein the negative stimulus deliverer is a loud noise.

Embodiment 12

The maze of embodiment 1, wherein the control system includes a proximity monitor to determine when the mouse enters the first room.

Embodiment 13

The maze of embodiment 1, wherein the control system monitors the number of negative stimuli delivered by the negative stimuli deliverer.

Embodiment 14

A process for evaluating a progression of Alzheimer's disease in a rodent model comprising:
  providing a maze;
  placing a rodent between the first and second rooms; and
  recording the number of times the rodent enters the first room; and
  determining an indication of the progression of Alzheimer's based on the number of times the rodent enters the first room.

Embodiment 15

The process of embodiment 14, wherein the maze comprises
  a first room;
  a second room, wherein the first and second room comprise floors and walls configured to allow a rodent to traverse between the rooms;
  a negative stimulus deliverer in the first room;
  a first visual marker in the first room and a second visual marker in the second room, wherein the first visual marker is different than the second visual marker; and
  a control system to power the negative stimulus deliverer.

Embodiment 16

The process of embodiment 14, wherein the indication is a scale.

Embodiment 17

The process of embodiment 14, wherein the indication is based on a threshold entry number of times.

Embodiment 18

The process of embodiment 14, wherein the indication is based on a comparison to a previously recorded number of times the rodent entered the first room.

Embodiment 19

A maze for evaluating a rodent, the maze comprising:
  a first room connected to a second room, the first and second room having floors, and walls;
  a wall plate gap behind at least two of the walls and a floor plate gap below at least two of the floors, wherein the first and second rooms include illumination gaps beneath the opaque plate gaps;
  a negative stimulus deliverer in the first room;
  a first visual marker in the first room and a second visual marker in the second room the first visual marker being different than the second visual marker; and
  a control system to power the negative stimulus deliverer.

Embodiment 20

The maze of embodiment 19, wherein the floor plate gaps include slots configured to receive an opaque plate.

Embodiment 21

The maze of embodiment 20, wherein the visual markers are opaque plates inserted in the floor or wall plate gaps, and each opaque plate has a different color or shade.

Embodiment 22

The maze of embodiment 19, wherein the illumination gaps include slots configured to receive an illumination plate that includes LEDs, a batter and a control system.

Embodiment 23

The maze of embodiment 19, wherein the walls and floors are comprised of transparent PMMA.

Embodiment 24

A system for diagnosing an Alzheimer's status of a human patient, the system comprising:
  a headset;
  a memory containing machine readable medium comprising machine executable code having stored thereon instructions for performing a method of displaying visual markers to a patient;
  a control system coupled to the memory, the control system configured to execute the machine executable code to cause the control system to:
    display, in the headset, visual markers to the patient;
    detect patient responses to the display of the visual markers; and
    determine, based on the patient responses, indication of the progression of Alzheimer's in the patient.

Embodiment 25

The system of embodiment 24, further comprising an actuator for receiving patient responses.

Embodiment 26

The system of embodiment 25, wherein the control system is configured to determine whether a patient depresses the actuator within a certain time after displaying the visual marker to the patient.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 19 depicts a table showing a percentage that is displayed in FIG. 18.

Figure 1:
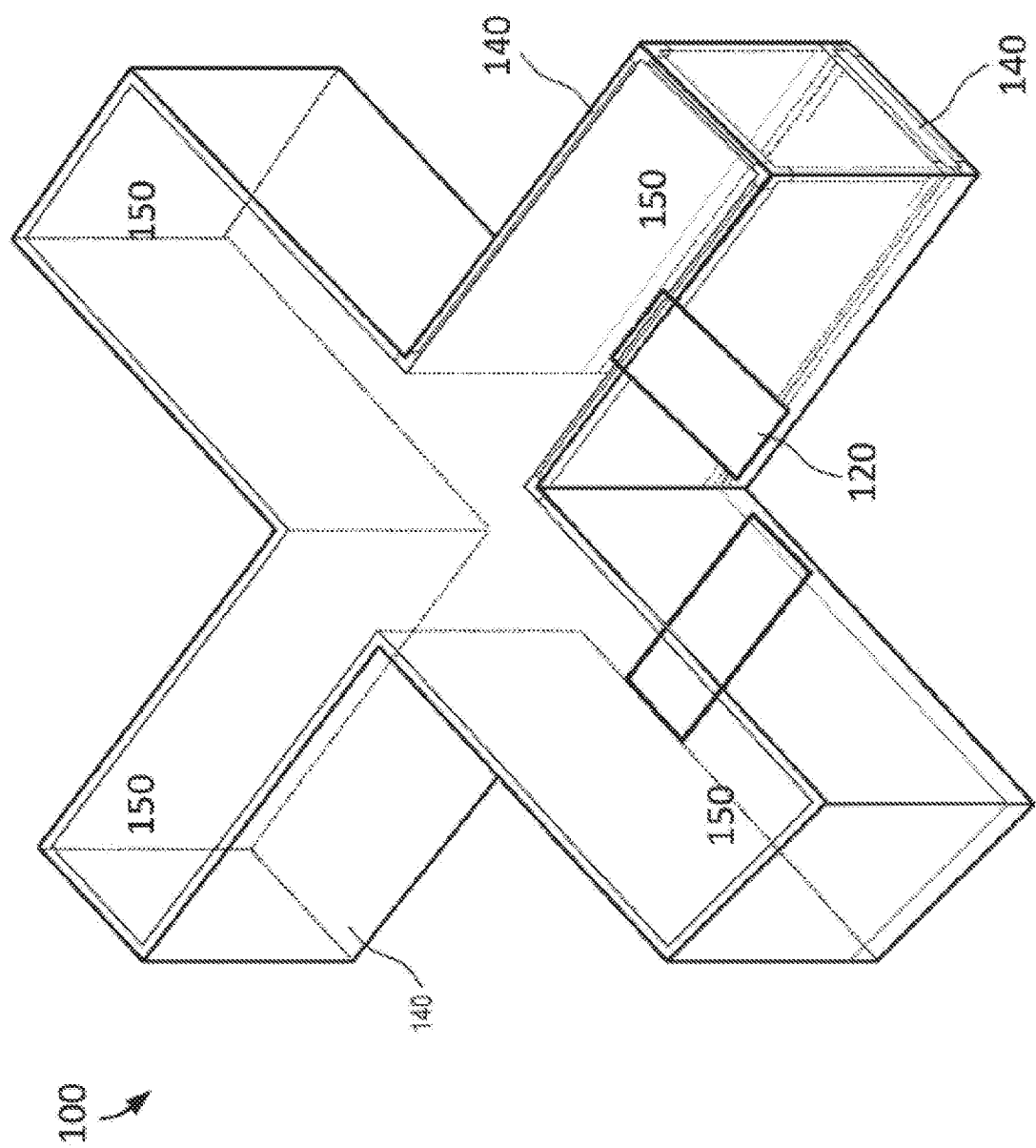
FIG. 1 depicts a perspective view of a maze that is constructed in accordance with the principles of the present disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Currently, reliable tools to diagnose Alzheimer's disease ("AD") at early stages (e.g., prior to cognitive decline) do not exist. For instance, the pathological hallmark of Alzheimer's, amyloid plaques, are generally limited to the brain and therefore difficult to screen and detect until manifestation of cognitive impairment systems. However, patients with AD also develop Aβ plaques in the retina and the inventors have discovered that these plaques are limited to certain regions of the retina. Therefore, presently disclosed device, system, and method provides a visual test that detects visual dysfunction associated with the areas of the retina affected in AD that may reliably screen for AD.

Accordingly, the maze of the present disclosure includes a rodent and human behavioral test for evaluating visual dysfunctions associated with the retinal changes in AD models. In one example of the present disclosure, the maze tests a rodent's ability to identify (1) specific contrasts, (2) specific colors, (3) certain items in the visual field, and (4) other 'non-typical' peripheral and night vision functions associated with AD. For instance, the maze may test the rodent's ability to avoid certain colors or contrasts gradients. The maze may include certain rooms with specific visual markers (e.g., colors, contrasts, objects or other visual features) that also contain shock plates.

Accordingly, if the rodent's visual function is normal, the rodent could learn which rooms, halls, or areas with certain visual markers are associated with the negative shock stimulus and avoid those rooms. Otherwise, if the rodent's visual function is impaired, and the visual markers cannot be identified, the rodent would re-enter rooms with visual markers known to be associated with shock anyway, and receive the shock stimulus. Accordingly, if the visual makers are designed to test retinal dysfunctions associated with AD, the inability of the rodent to distinguish the visual markers and entering rooms with shock associated visual markers would indicate that rodent has developed retinal plaques associated with AD or that could be associated with AD.

FIG. 1 illustrates an example of a maze 100 (or container or other environment) constructed in according to principles of the present disclosure. In some examples, maze 100 may be a maze for a rodent built of a physical walls and hallways for a rodent to walk around, or may be a virtual reality environment for a subject.

For instance, the maze 100 may be a rodent maze with walls made of PMMA, PDMS, (e.g. PMMA), or plastics or other convenient materials. For instance, the maze 100 may include several different walls of PMMA that are constructed together to form passageways for the rodent to walk. In some examples, the walls will be made of a clear plastic like PMMA so that various visual markers can be connected or illuminated from the outside so that the rodent can see them through the transparent PMMA.

In other examples, maze 100 may be a virtual reality environment that are projected to a patient through a virtual reality headset, and may include various walls and other features as necessary. The headset may communicate audio instructions or feedback to the user through the head set. Headset may be any suitable headset to display the features disclosed herein including the Samsung Gear VR powered by Oculus available at http://www.samsung.com/global/galaxy/wearables/gear-vr/. Although the embodiment regarding the mouse maze 100 is discussed herein, this is included and mentioned through to indicate all of these concepts could be applied or adapted to a virtual reality environment for a human subject.

The maze 100 may include various rooms 150 which may be areas, hallways, or other demarcations of the maze 100. As illustrated in FIG. 1, the maze 100 may be a series of four rooms 150 that are rectangular and connected to a central area to form a cross. In the illustrated example, the four rooms 150 meet at the center at 90 degree angles. This is advantageous, because a rodent (or human) placed at the center of the maze 100 can see fully down each room 150 by turning their head. In other examples, the rooms 150 may be tubular or other suitable shapes or could meet at different angles.

In some examples, the maze 100 may include only three rooms 150 that meet at 120 degree angles or other suitable angles. In still other examples, the maze 100 may only include two rooms 150 and be one long rectangle, or may form an angle (e.g., 90 degrees, 30 degrees, and the like) and form a V shape instead.

Rooms 150 may be a separate compartment or area, or may be a small barrier or section of a compartment. Rooms could be a portion of a hallway, and may be any other physical location in the maze 100 that may be associated with a particular visual marker.

Furthermore, the maze 100 could be any other combination of rooms 150 that includes a circular maze with radial passages, a maze that includes vertical or diagonally oriented rooms 150 and other passageways.

Also illustrated in FIG. 1 is negative stimulus deliverer 120. For instance, negative stimulus deliverer 120 may include a shock plate or metal prongs to deliver a shock, a capsaicin spray, may include a proximity detector that links to trigger a loud sound when a rodent or subject comes within close proximity. In some examples, the maze 100 may not include a negative stimulus deliverer 120 and rather may include audible instructions to a user in a virtual reality environment.

The dimensions of the maze 100 may include any suitable dimensions to adequately perform the visual tests, including field of view. As illustrated, the maze 100 may have a height "H", width "W", and long diameter "D" that may be a physical distance for a rodent maze or may be a perceived distance for a virtual reality environment. For instance, W may be 10 cm, H may be 15 cm, and D may be 100 cm.

In examples where maze 100 is a PMMA or other physical structure for a rodent, maze 100 may include slots 140 for inserting visual markers. The slots 140 may be a slot that may be a space with guide rails or other mechanical features to retain a colored tab to change the color of the walls. In some examples, this will be particularly useful with a transparent maze walls or room 150 walls that allow the color tabs to be secured to the outside but still seen by the rodent through the transparent maze 100. In some examples, the slots 140 may be on each of the wall including the top, sides and bottom. In other examples, the slots 140 may only be on the bottom and sides.

Figure 2:
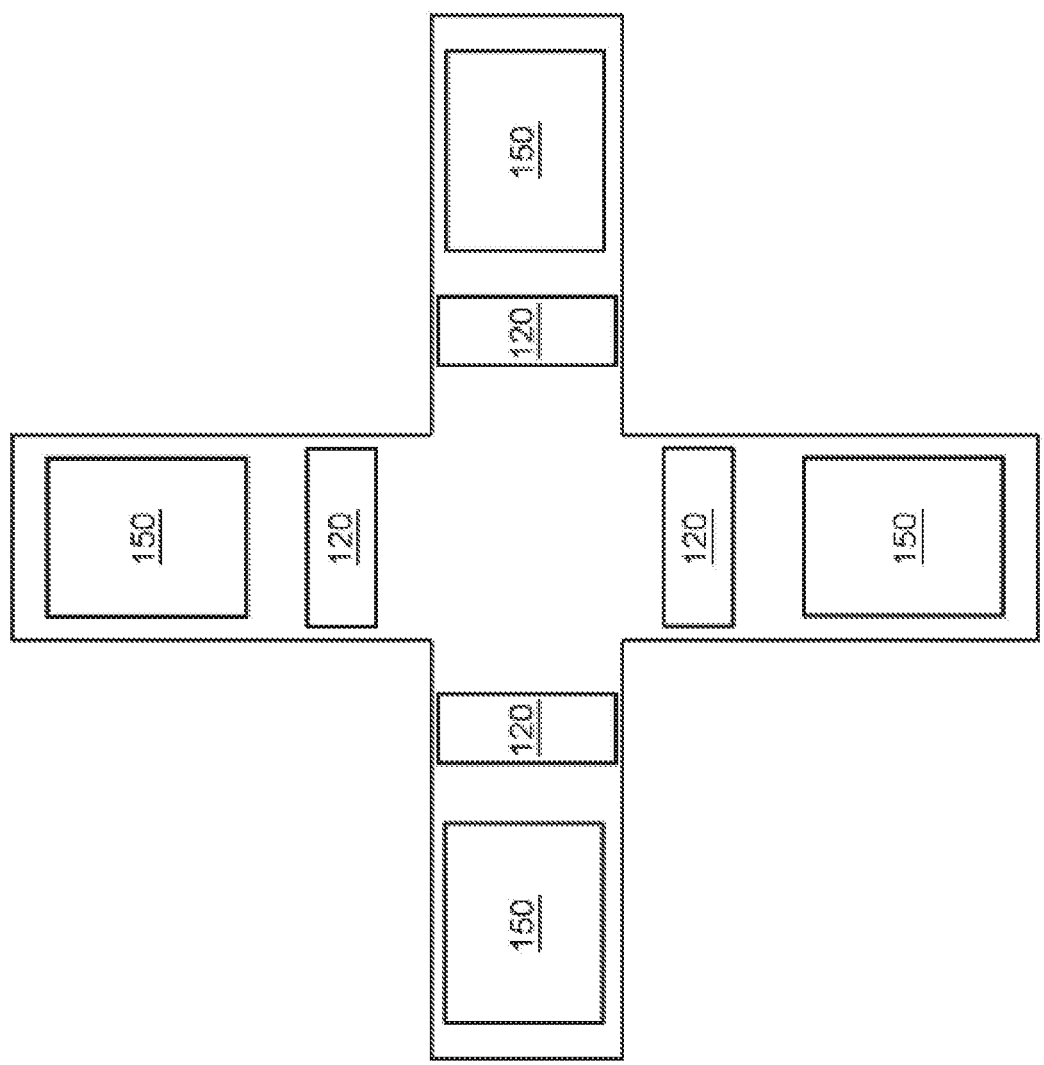
FIG. 2 depicts a top view of a maze with colored visual markers that is constructed in accordance with the principles of the present disclosure.
Figure 3:
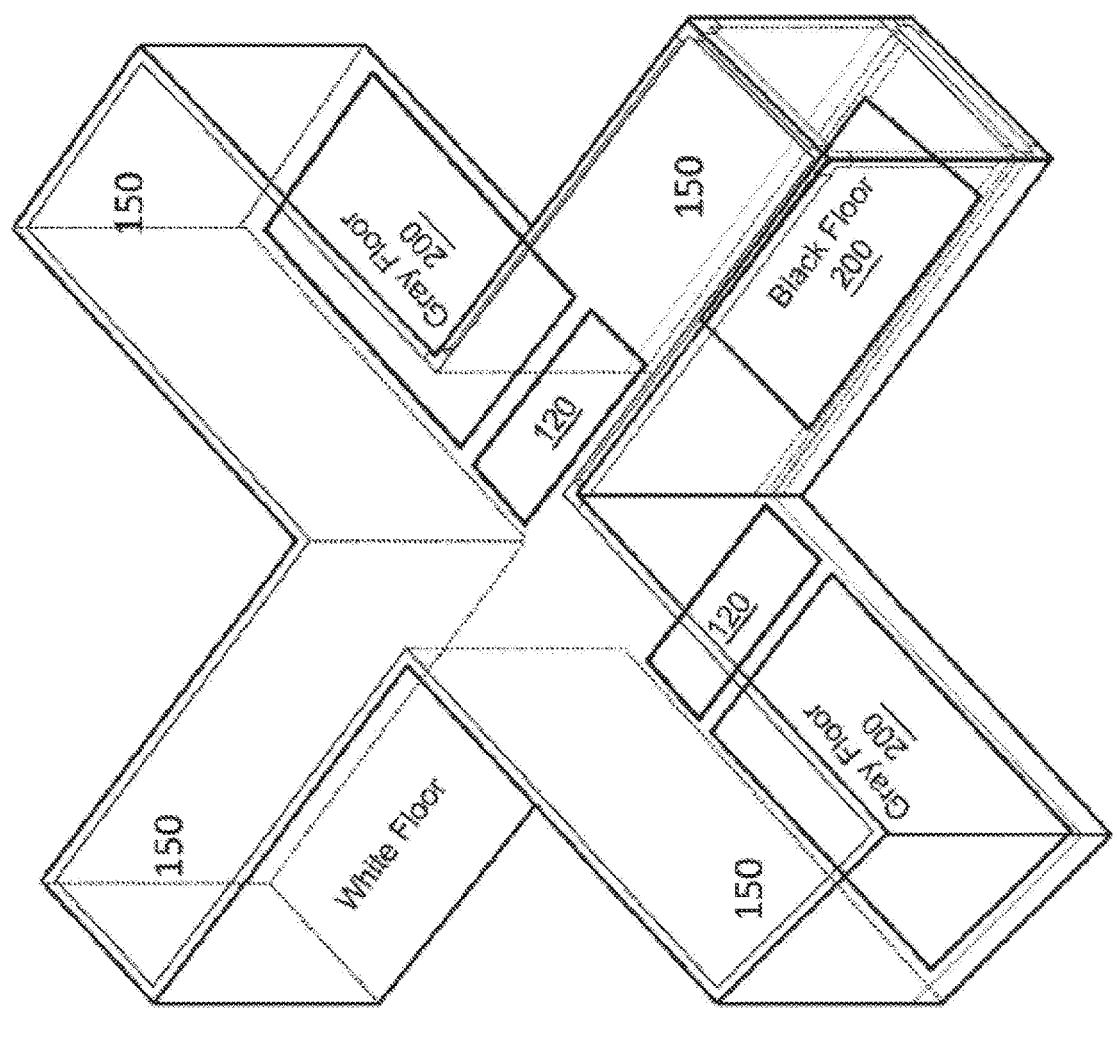
FIG. 3 depicts a perspective view of a maze with black and grey floors that is constructed in accordance with the principles of the present disclosure.

FIGS. 2 and 3 illustrate an example of the maze 100 that includes various visual markers 200 that may be colored, including by illumination or tab insertion. For example, each room 150 may contain a different visual marker 200 (e.g., red, blue, grey, white) that may illuminate the entire room 150, or may include strips of colored LEDs that illuminate the room 150 from compartments outside the walls. In this example illustrated in FIG. 2, a rodent or subject would have options of going to the red room 150, blue room 150, white room 150 or grey room 150.

Additionally, each room 150 may include a shock plate or other negative stimulus delivery apparatus 120 that blocks the entrance to the room 150 or is inside the room. In the example of the rodent maze 100, a shock plate or prongs 120 may be just before the entry to the room 150 or where the visual marker 200 begins. In some examples, the shock plate 120 may be placed in a position near where the colored LED begins to illuminate the room 150 if you are approaching the room from the center. Thus, there may be a certain distance "x" prior to the shock plate 120 or other negative stimulus delivery device 120 from the center of the maze 100 towards the room 150 to allow the mouse a certain amount of leeway or distance to turn around, etc.

In some examples, the negative stimulus device 120 may be turned on and off by a control system. The control system may be a wired or wireless device that controls the illumination of the markers (200) and/or turns on and off the negative stimulus delivery devices 120. In some examples, simply turning on the maze 100 turns on set markers 200 (e.g., LEDs) and turns on negative stimulus delivery devices 120 in certain rooms 150. Control system may be any suitable process and memory combination with appropriate connections to operate the LEDs and energize and deliver a suitable shock to a rodent.

FIG. 3 illustrates an additional maze 100 that utilizes visual markers 200 that test contrast recognition of the rodent. For instance, the maze 100 may have visual markers that are, for example, colored inserts or LEDs that separately light up the wall and floor different colors. As an example, one of the rooms 150 may have a grey floor 200 against white walls 200 (low contrast), and another may have a black floor 200 against white walls 200 (high contrast).

In this example, the rooms 150 with grey floors 200 against white walls 200 may be the forbidden rooms 150 and therefore the control system may energize the shock plates 120 that block the entrance to those rooms 150. Therefore a rodent may learn not to enter the low contrast rooms 150 over time if they can distinguish between the contrast differences in greyscale. The same concept could be performed with different shades of the same color on different walls or different portions of the wall or room 150.

Figure 4:
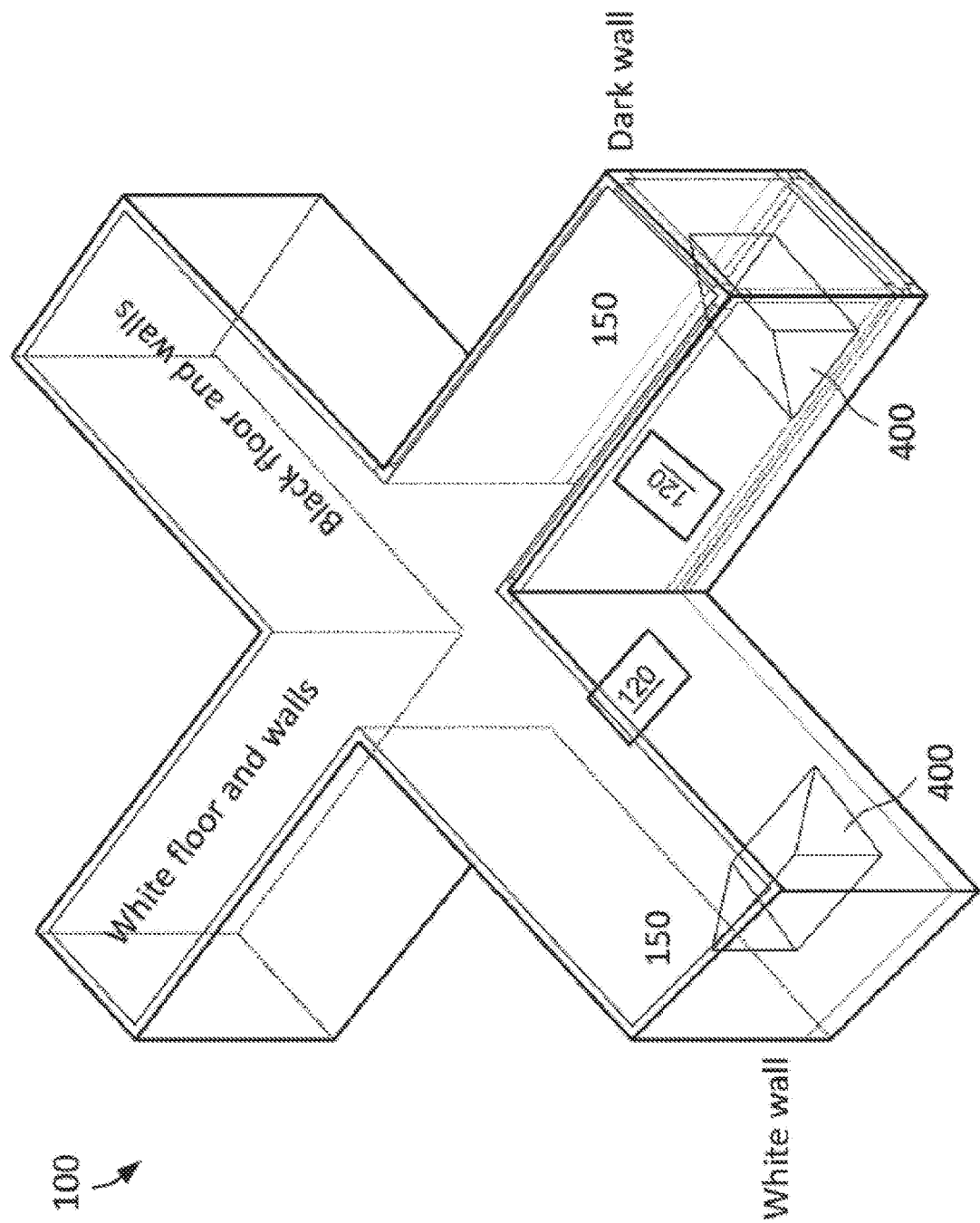
FIG. 4 depicts a perspective view of a maze with a ramp that is constructed in accordance with the principles of the present disclosure.

Referring to FIGS. 3-4 concurrently, FIG. 4 illustrates an example that utilizes physical structures 400 in combination with visual markers 200. For instance, one of the rooms 150 may have a physical structure 400 that is colored black 200 or has a certain color of LED illuminating 200 it. In another room 150, the same physical structure 400 may be present, but may be white 200 or have some other color illuminating it. Physical structures 400 may be stairs, platforms or other visual features.

Figure 5:
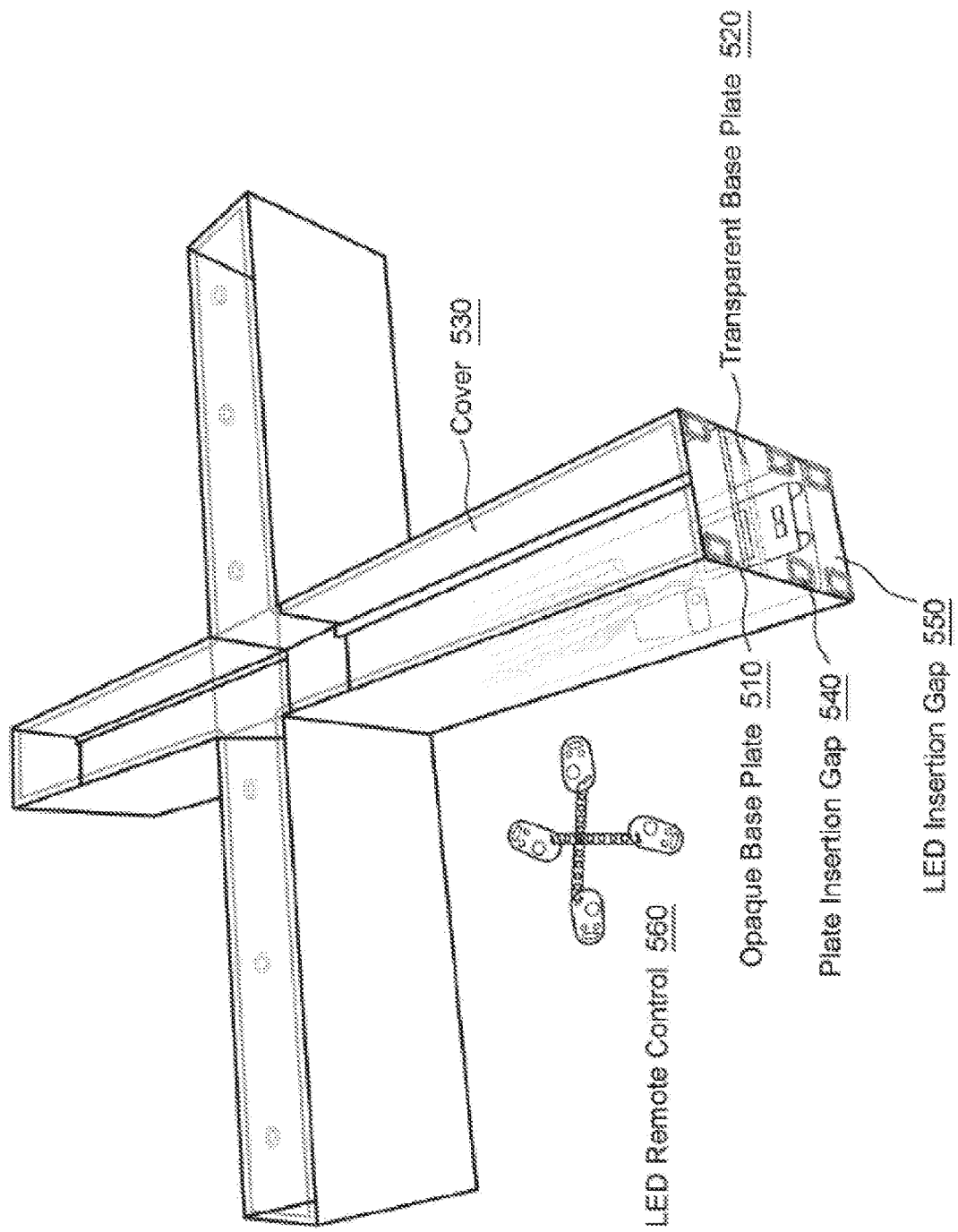
FIG. 5 depicts a perspective view of a maze with an opaque plate gap and illumination gap that is constructed in accordance with the principles of the present disclosure.

FIG. 5 is an overview of an example of a maze 100 that includes dark walls that are all of the same color but includes plate insertion gap 540 for insertion of an opaque plate 510 and an illumination insertion gap 550 for the insertion of a lighted visual marker 200 such as an LED, or other colored light source. Furthermore, here the control system may communicate with light source remote control 560 which may, include a button or separate indicator for each light strip.

Accordingly, in this example, the visual indicator is presented through a transparent base plate 520 which the rodent would walk on top of and then colored plates may be inserted into the plate insertion gap 540 or LED or other light strings may be placed into the illumination gap 550. Therefore, in this example, each of the floors of the different rooms 150 may be illuminated or placed with an opaque plate 510 of different color to perform the disclosed tests.

Figure 6:
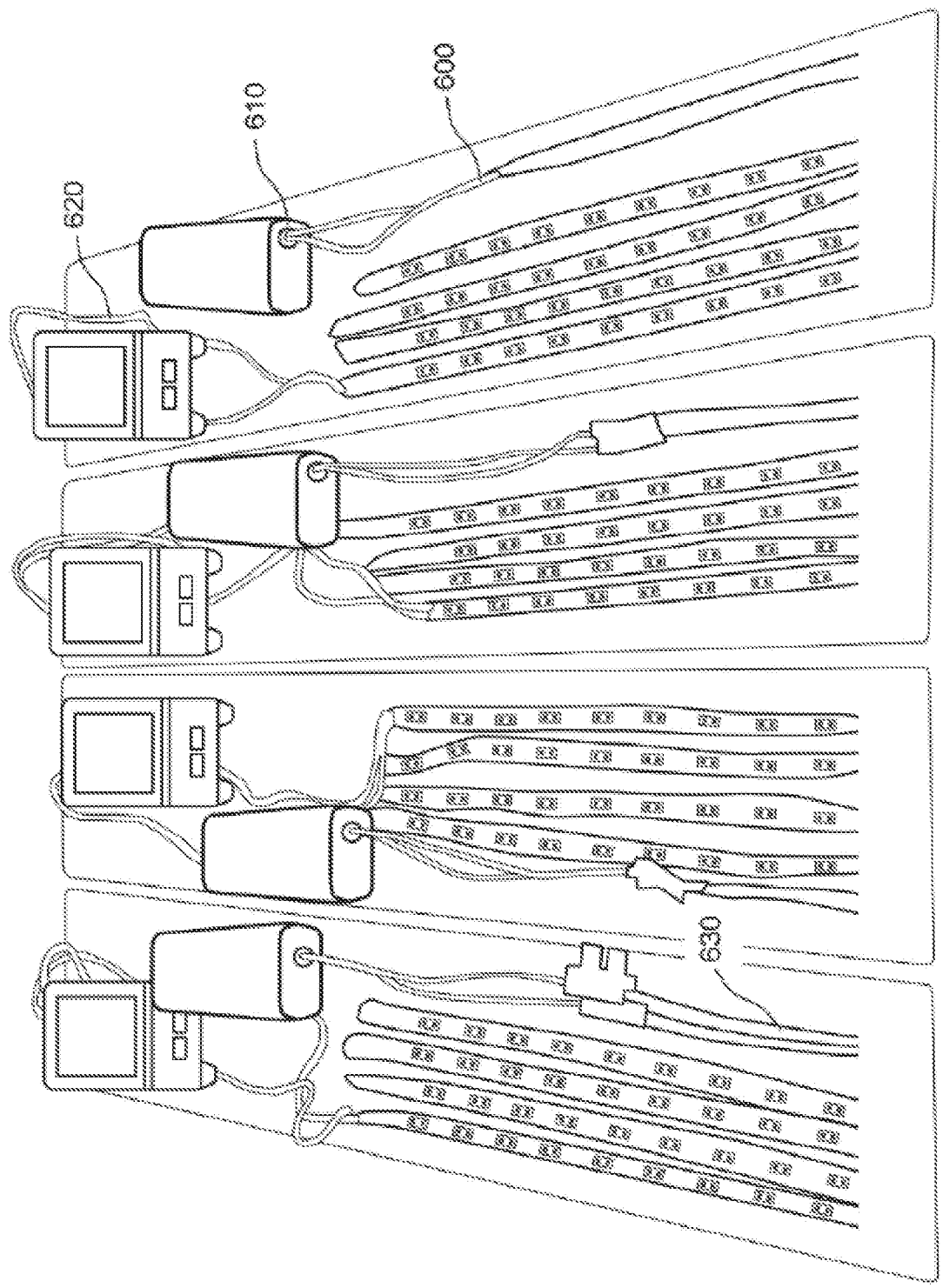
FIG. 6 depicts a perspective view illumination plates with LEDs attached to a control system that is constructed in accordance with the principles of the present disclosure.

FIG. 6 illustrates an example of illumination plates 600 that includes LED strips 630 for example connected to an LED driver 620 and battery system 610. Accordingly, in some examples, a plate (for example of PMMA or other suitable material) may contain LED strips 630 that are fixed to the plate so that the run the majority of the length of the plate. In some examples, each plate may have a different color of LED attached or other light source. In other examples, the LED may have a dimmer, be capable of emitting different colors or have other suitable and relevant functionality. In some example, other types of lights may be utilized.

Thus, the illumination plates 600 illustrated in FIG. 6 may be inserted into the illumination gap 550 illustrated in FIG. 5. Thus, various plates may be swapped out of the illumination gap 500 to provide different colors, contrasts or other functionality as needed.

Figure 7:
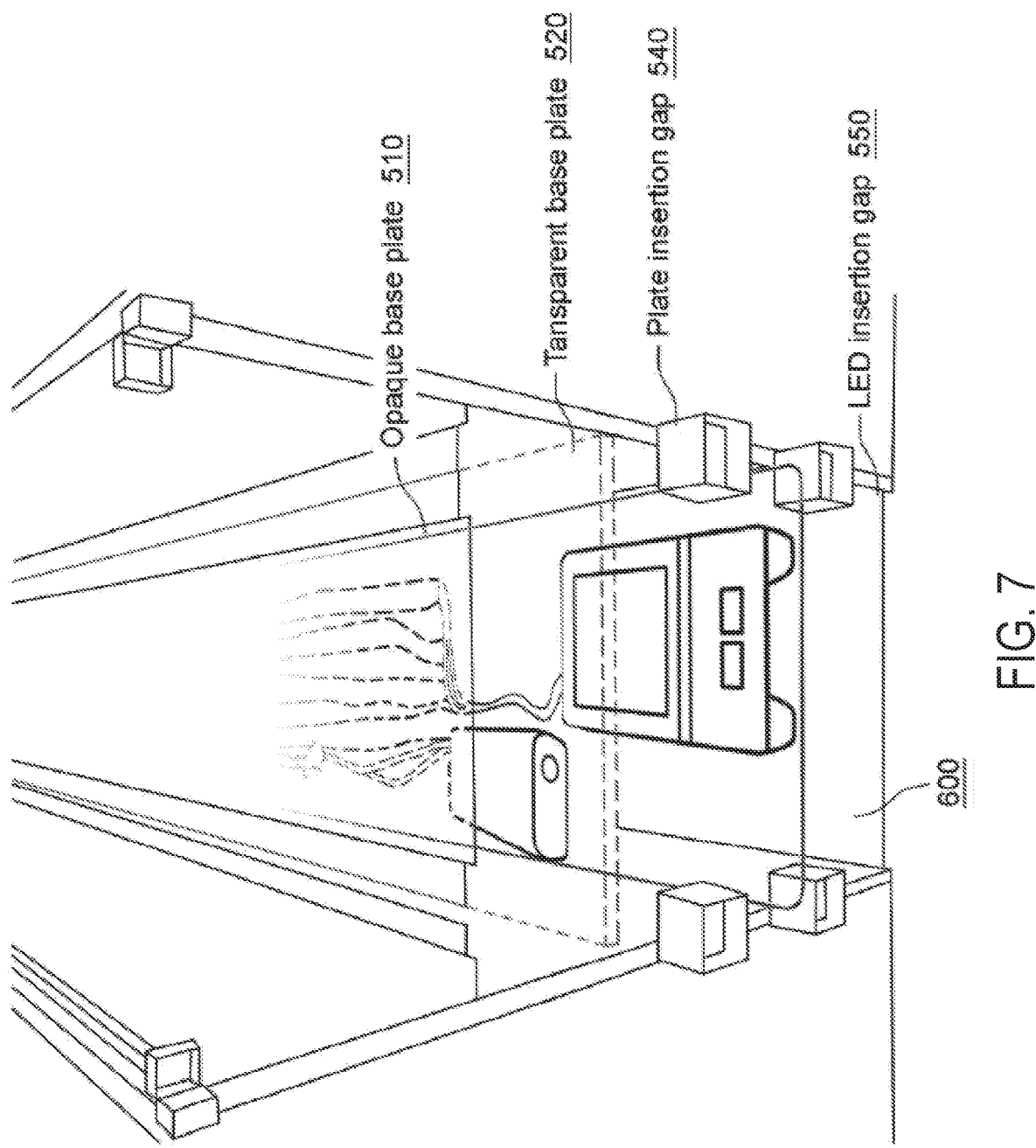
FIG. 7 depicts a perspective view of an end of a room with an opaque plate gap and illumination gap that is constructed in accordance with the principles of the present disclosure.

FIG. 7 illustrates a close up view of the end of room 150 illustrated in FIG. 6 that includes the transparent base plate 520 that the rodent may walk along, the plate insertion gap 540 for inserting an opaque plate 510. As illustrated, the opaque plate 510 is inserted inside the insertion gap 540 just underneath the transparent base plate 520. In some examples, different colored, white or black opaque base plates 510 may be inserted by a technician into the insertion gap 540.

Additionally, illumination plate 600 may be inserted into the illumination gap 550. Accordingly, in this example, illumination gap 550 is a relatively large compartment underneath the transparent base plate 520 and opaque base plate 510 to allow the illumination plate 600 which includes the electronics and for example LED strips to fit underneath.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example 1: Diagnostic Process for Rodent Models

Figure 8:
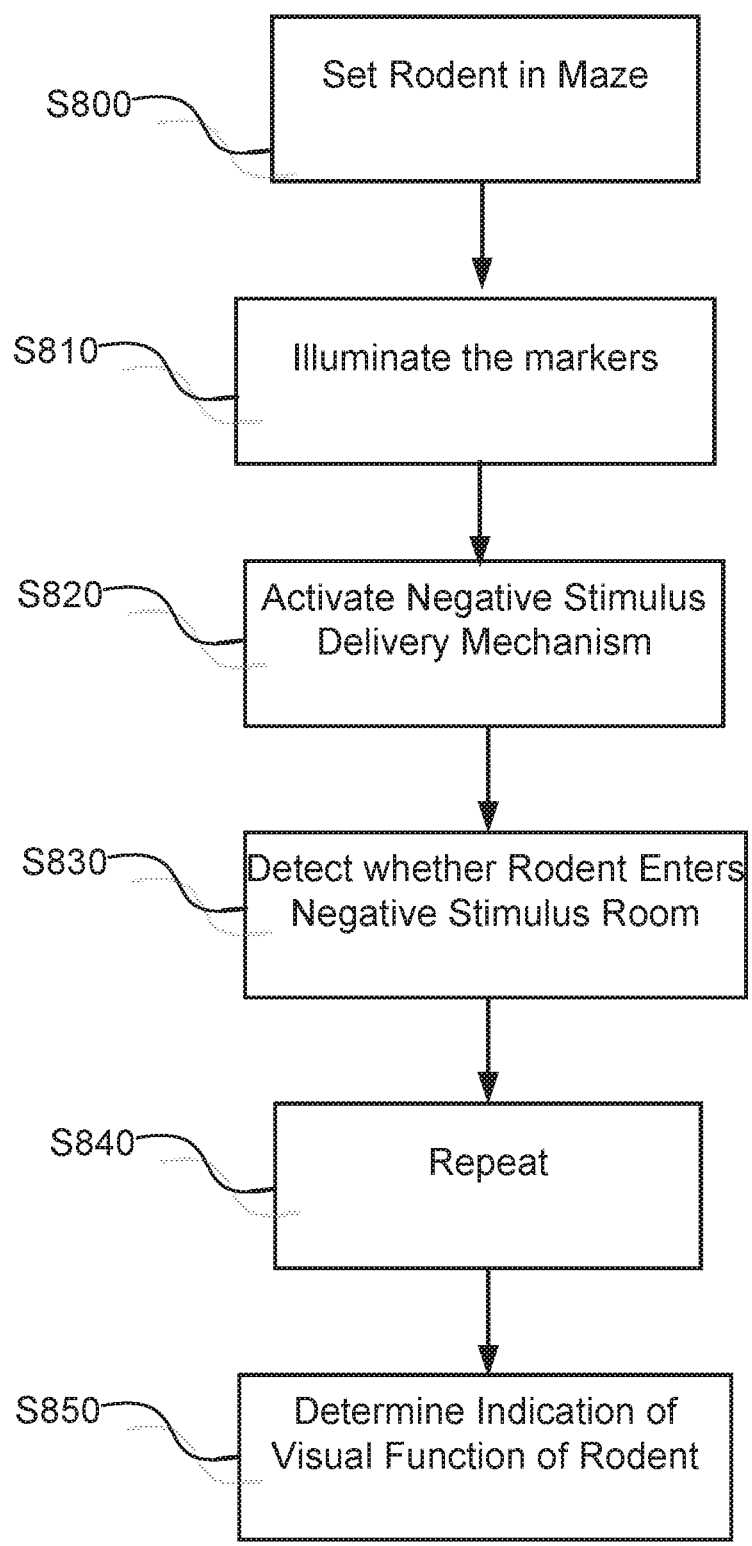
FIG. 8 depicts a flow chart depicting a process for diagnosing a progression of AD in a rodent model that is constructed in accordance with the principles of the present disclosure.

FIG. 8 illustrates an example process for using the disclosed maze 100 to diagnose Alzheimer's disease and monitor the progression of the disease in rodents. For instance, in some embodiments, the rodent will be first placed in the maze to initiate the test (S800). In some examples, that will be in the center of the maze 100 if the rooms 150 all are connected to the center portion.

Next (or before the rodent is placed in the maze 100) the markers will be illuminated (S810) and any negative stimulus delivery mechanism will be activated and powered up (S820).

Then, either a technician or proximity sensor will detect whether the rodent enters the negative stimulus room (S830). In some examples, this will include the amount of times the rodent enters, the amount of time before the rodent enters and gets shocked, or potentially a number of times the rodent is shocked by counting discharges of the negative stimulus delivery device.

Then, the experiment may be repeated a certain number of times or to train the rodent (S840). Accordingly, once sufficient runs have been performed with the rodent, the number of negative stimulus activations and other parameters surrounding the rodent's entry into the forbidden rooms will be processed to determination an indication of visual function of the rodent (S850).

Accordingly, the data may be fed to a control system for a particular rodent, which will evaluate the number of times the rodent enters the forbidden room, and may either: (1) determine if it crosses a threshold for that particular visional dysfunction being tested and/or (2) compare it to previous testing for the same visual dysfunction and determine whether there is a significant increase for that particular rodent. Accordingly, in some example the indication may be a yes or no, it may be a score based on that particular test or rodent that indicate a progression of AD.

Example 2: Rodent Maze

In one example of the present disclosure, the maze 100 may include four rooms 100 (e.g., 45 cm long, 10 cm long, and the like) extending from a central arena (10×10 cm). The rooms 150 may be angled at 90° to each other, yielding a plus shape. All four rooms 150 of the maze (45×10 cm) may include black sidewalls (15 cm high). The maze 100 may be elevated on a tripod 70 cm above the floor. A different LED array of lights (e.g., Blue, Red, Green, White, and the like) may be positioned on the floors of each room 150 near the room 150's end. Each LED included a dimmer, which enabled intensity optimization.

Using this example maze 100, a test at various light intensities was carried out throughout the study. Light intensities are measured using a light meter (Zico-Zi-7811) two centimeters from the edge of the room 150 at the same height as the mouse is positioned. In addition changing floor color platform and triangular platforms are creating different inferior field contrasts.

Example 3: Color Distinction Paradigm

In some examples, a rodent may be trained and tested on a maze for color distinction. For instance, referring to FIGS. 1-3, each rodent may be assigned a color, and if that rodent enters a room 150 with that visual marker 200 color, the rodent will receive the negative stimulus (e.g., shock). The first trial will be without shock, the second and third trials will use shock or other negative stimulus for the training session. The rodent may then be tested again 840 in six weeks to test the decline in color distinction.

Example 4: Contrast Distinction Paradigm

In some examples, a rodent may be trained and tested on a maze for contrast distinction. In this example, two rooms 150 may include dark grey floors against black walls and be the forbidden rooms 150. One room 150 may include a white floor against the black walls (high contrast room 150). One room 150 may include a black floor against black walls (no contrast room 150).

Accordingly, the rodent may receive the negative stimulus (e.g. shock) if the enter the forbidden rooms. The first trial may be without shock, the second and third trials may use shock or other negative stimulus for the training session. The rodent may then be tested again 840 in six weeks to test the decline in contrast distinction.

Example 5: Contrast Object Distinction Paradigm

In some examples, a rodent may be trained and tested on a maze for contrast distinction. In this example, one room 150 may include a dark black object (e.g., stairs or platform) against black walls and one room 150 may include a white object (e.g., white stairs or platform) against a white wall. Both of these rooms may be the forbidden rooms 150. The area behind the stair may also serve as an escape place.

Accordingly, the rodent may receive the negative stimulus (e.g. shock) if the rodent enters the forbidden rooms 150. The first trial may be without shock, the second and third trials may use shock or other negative stimulus for the training session. Additional tests may be performed using a light gray object. The rodent may then be tested again in six weeks to test the decline in contrast distinction.

Example 6: Device for Humans to Detect Alzheimer's

Figure 9:
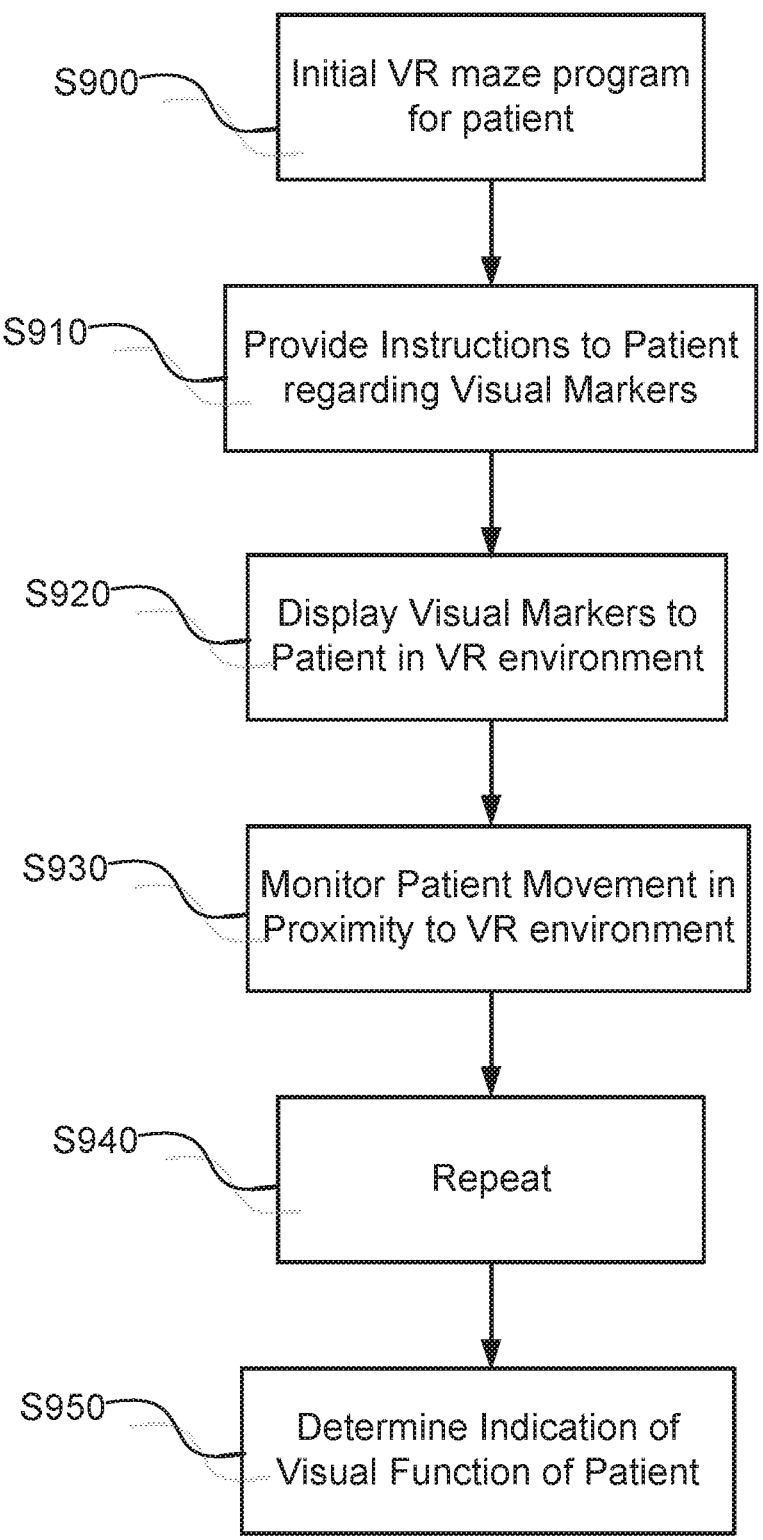
FIG. 9 depicts a flow chart depicting a process for diagnosing a progression of AD in a human mode that is constructed in accordance with the principles of the present disclosure.

FIG. 9 illustrates an example process for applying the visual test to a human subject that is screening for AD or testing the progression of AD. For instance, a clinician may place a VR headset on a patient and initialize the VR program 900. Then, the patient may receive instructions 910 from the VR headset audio device, or from the clinician on where to walk in the virtual maze in relation to the visual markers. For instance, the clinician may instruct the patient to walk towards or away from certain visual markers 200 or down certain virtual rooms 150 with specific visual markers 200.

Then, the virtual reality system will display visual markers 200 to the patient in a virtual reality environment 920. In some example, the virtual reality environment may mimic or closely approximate the physical rodent maze 100, but will not require actual negative stimulus as the patient instructions 910 will provide the basis for whether or not the patient can properly identify certain markers 200. Then, the VR system will monitor the patient's movement through the VR environment, and monitor the proximity of the patient with respect to the visual markers 930 based on the instructions. The test may be repeated a few times 940 to ensure the results are accurate and then the system may determine an indication of the visual function of the patient 950.

Accordingly, the visual markers 200 will migrate in the patient's field of view and can be placed at certain positions using certain contrasts to test the patient's visual function. Accordingly, the tests will evaluate the patient's visual function 950 as described above with respect to the rodent test.

In other examples, the device may be a stationary or other device that displays visual markers 200 in a patient's field of view, without showing virtual reality scenes to the patient. For instance, the device may be a device (goggles, headset, or larger stationary apparatus) into which a patient may insert their head. The device may then display visual markers 200 at certain angles with certain colors to test the same functions, and the patient may be instructed to click a button when they see colors, certain colors, or visual markers 200 at certain positions.

These visual markers 200 may be displayed to the patient at certain angles or in certain section of their field of view to test the same or similar visual function as tested on the rodents above. Accordingly, this system could be implemented in a variety of ways to diagnose potential Alzheimer's in a human model.

Example 7: Test Results to Evaluate Visual Preferences Between Wild Type and Transgenic Alzheimer's Disease Model Mice The inventors performed an example protocol to establish a custom-tailored behavioral test in order to evaluate visual field and color distinction in APP/PS1 transgenic mice (AD model) compared to their wild-type counterparts C57bl/6 strain.

Modified Plus Maze testing was performed according to SOP 132 "Visual Stimuli Plus Maze": The custom-made plus maze consisted of four arms (45 cm long) extending from a central arena (10×10 cm). The arms were angled at 90° to each other, yielding a plus shape. All four arms of the maze (45×10 cm) had black sidewalls (15 cm high). The maze was elevated on a tripod 70 cm above the floor. A different LED array of lights (Blue, Red, Green, White) was positioned on the floors of each arm near the arm's end. Each LED has a dimmer which enabled intensity optimization. The test was performed at various light intensities throughout the study. Light intensities were measured using a light meter (Zico-Zi-7811) two centimeters from the edge of the arm at the same height as the mouse was positioned.

Transgenic mice and their Wild Type (WT) counterparts were acclimated to the maze at maximum light intensity during one trial and baseline measurements were acquired for all mice. The results are displayed in Table 1 and include a total of 10 transgenic and 8 WT mice aged 10-15 months.

TABLE 1

Visual plus maze baseline trial, time spent in each arm

| Light inten-sity | Percent of time spent in each arm Mice Strain | | | | | | | |
|---|---|---|---|---|---|---|---|---|
| | AAP/PS1 mice | | | | WT counterpart | | | |
| | White | Red | Blue | Green | White | Red | Blue | Green |
| Max | 9.60 | 53.70 | 12.60 | 11.40 | 11.33 | 43.83 | 11.63 | 12.71 |
| High | 9.27 | 68.33 | 5.03 | 5.70 | 7.54 | 59.08 | 7.17 | 11.38 |
| Mid | 6.60 | 62.50 | 7.93 | 15.57 | 5.46 | 66.88 | 8.33 | 9.25 |

Similarly to young mice, the old mice (both APP/PS1 transgenic and their wild-type counterparts) exhibited preference to the Red arm with no clear distinction between the other three arms. The preference in old mice was somewhat more pronounced compare to the young mice.

Light intensities were then decreased to Low level and two additional trials were performed. These trials resulted again in a preference to the Red arm but showed a reduction in preference with low light intensities in the WT mice group. At these intensity levels, WT mice lost the preference of Red versus White arm, while transgenic mice retained it, as shown in Table 2.

TABLE 2

Visual plus maze second and third trials

| | | Percent of time spent in each arm | | | | | | | |
|---|---|---|---|---|---|---|---|---|---|
| Mice | Light | Second Trial | | | | Third Trial | | | |
| Strain | intensity | White | Red | Blue | Green | White | Red | Blue | Green |
| APP/PS1 | High | 12.43 | 36.70 | 14.53 | 29.03 | 15.17 | 22.83 | 31.10 | 21.30 |
| transgenic | Mid | 13.10 | 27.53 | 16.67 | 35.33 | 6.97 | 46.37 | 26.27 | 14.97 |
| | Low | 20.40 | 46.23 | 16.40 | 13.77 | 19.87 | 28.00 | 37.27 | 11.07 |
| WT | High | 9.50 | 39.13 | 19.71 | 21.04 | 15.88 | 45.58 | 15.17 | 18.21 |
| counterpart | Mid | 19.29 | 41.92 | 6.71 | 25.83 | 7.54 | 33.29 | 39.13 | 15.13 |
| | Low | 32.71 | 24.04 | 20.83 | 19.38 | 33.00 | 23.33 | 24.79 | 16.71 |

Figure 10:
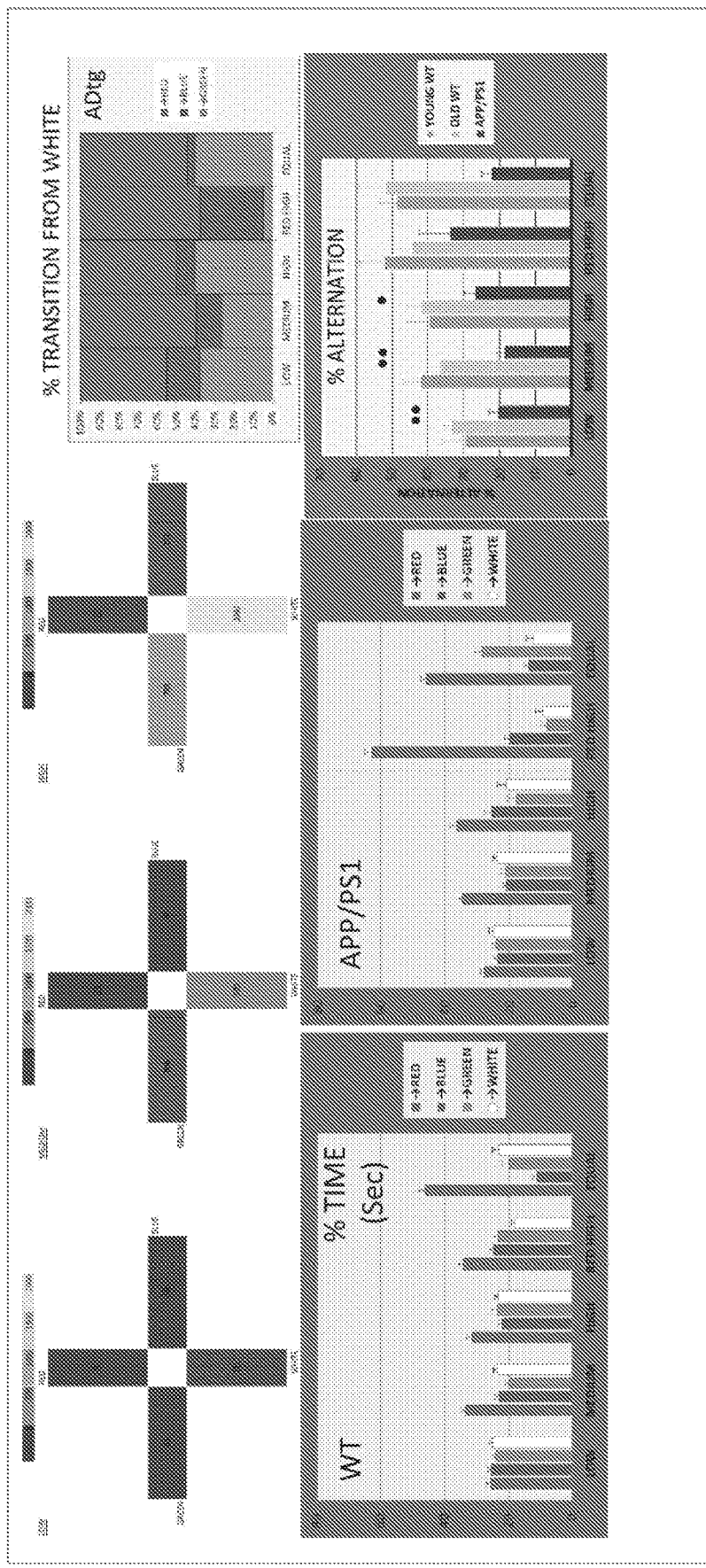
FIG. 10 depicts results of a visual stimuli test in ADtg mice that uses a maze that is constructed in accordance with the principles of the present disclosure.

Example 8: Test Results to Evaluate Visual Preferences of Transgenic Alzheimer's Disease Model Mice FIG. 10 depicts results of a visual stimuli experiment in adiponectin-overexpressing (ADtg) mice that uses a maze that is constructed in accordance with the principles of the present disclosure. This experiment (as shown in, e.g., FIGS. 11-16) tested various aspects of peripheral-inferior vision in ADtg mice versus age and sex-matched healthy control mice were tested using custom-made Plus Maze apparatus. The experiment includes 5 light intensity conditions and 4 colors in the inferior visual field to detect retinal-related deficits specific to ADtg mice. The experiment also included a use of diverse wavelengths and intensities in visual field in custom-made plus maze. The results measure visual/functional deficits in animal models of AD, during disease progression and in response to therapy. The results may also guide translation and development of a virtual reality (VR)/augmented reality (AR) application designed for human patients.

Figure 11:
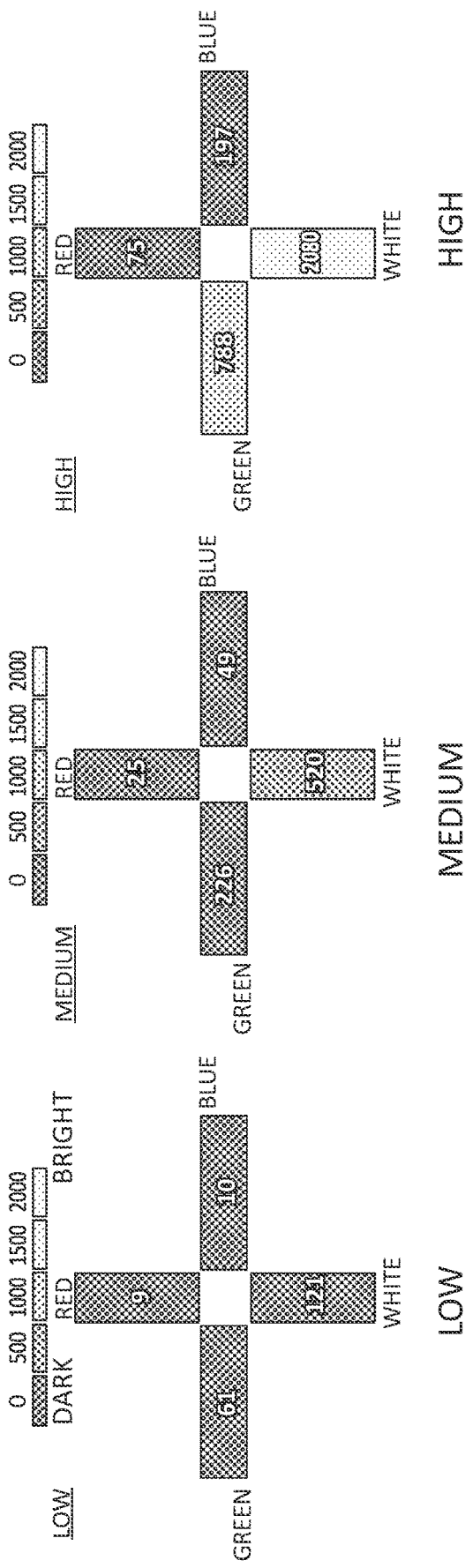
FIG. 11 depicts an example of a visual stimuli test in ADtg mice including a maze with a visual marker that is constructed in accordance with the principles of the present disclosure.

FIG. 11 depicts an example of a visual stimuli test in ADtg mice including a maze with a visual marker that is constructed in accordance with the principles of the present disclosure. The maze may include a color intensity of, e.g., low, medium, high, red high, or equal. The intensity was measured with lumniometer, wherein LUX is equal to $2.5*2^{(ev)}$. The intensity is in following order of colors: red, blue, green, and white.

Figure 12:
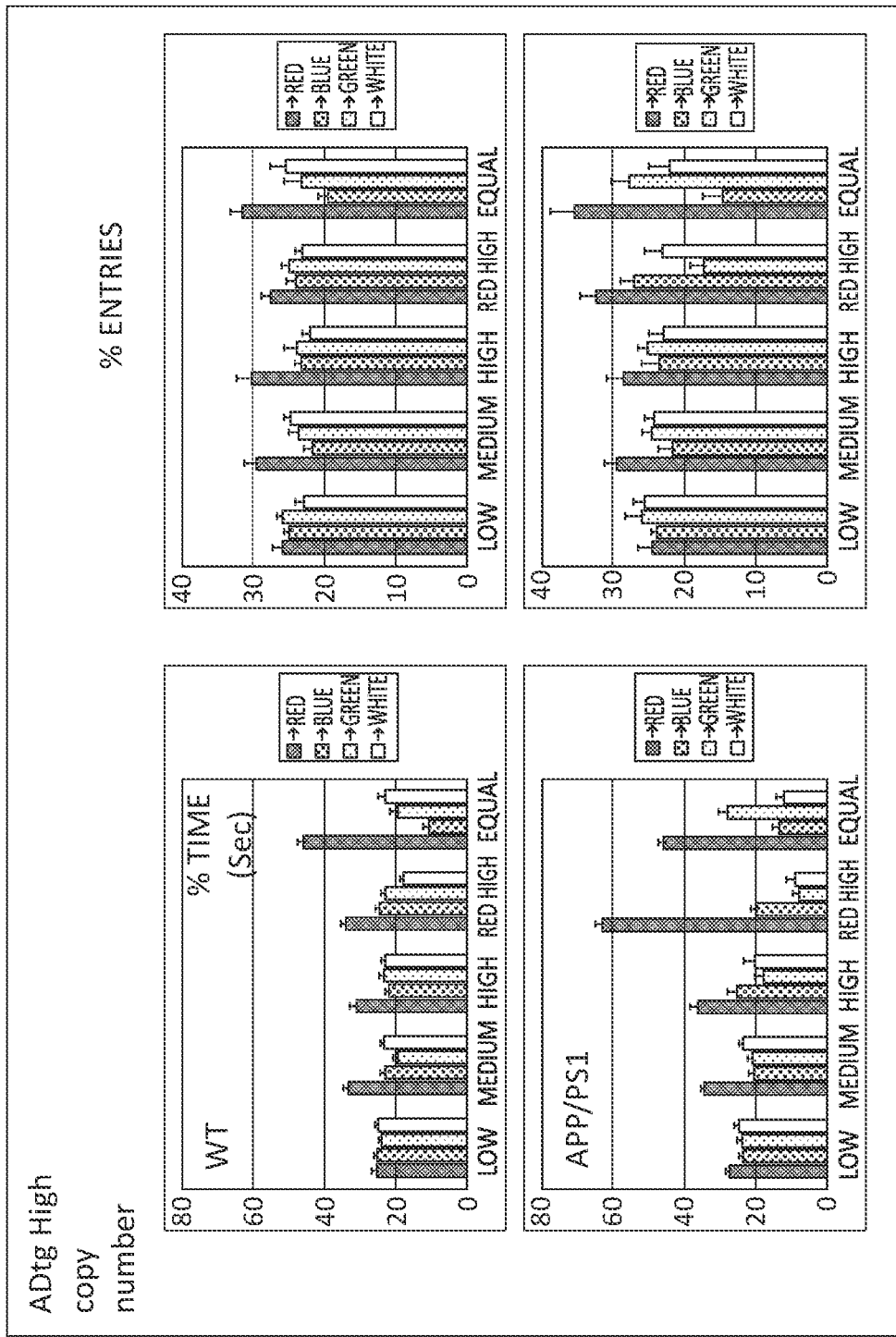
FIG. 12 depicts results of a visual stimuli test in ADtg mice that uses a maze of FIG. 11.
Figure 13:
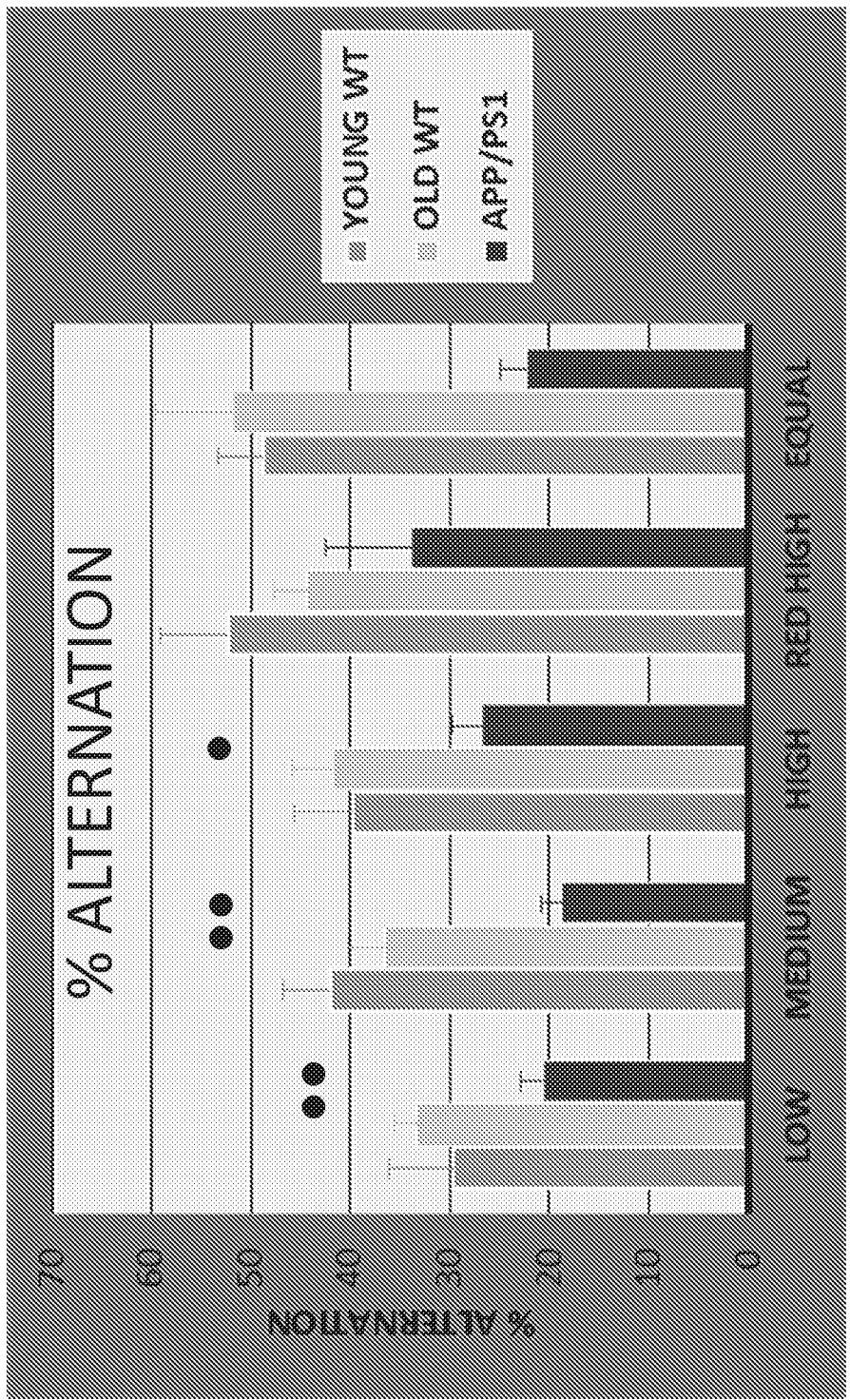
FIG. 13 depicts differences in percentage of alternation between wildtype and APP/PS1 transgenic mice in results of visual stimuli test that uses a maze of FIG. 11.

FIG. 12 depicts results of a visual stimuli test in ADtg mice that uses a maze of FIG. 11. FIG. 13 depicts differences in percentage of alternation between wildtype and APP/PS1 transgenic mice in results of visual stimuli test that uses a maze of FIG. 11. The difference in percentage of alternation includes differences in memory and color/intensity discrimination.

Figure 14:
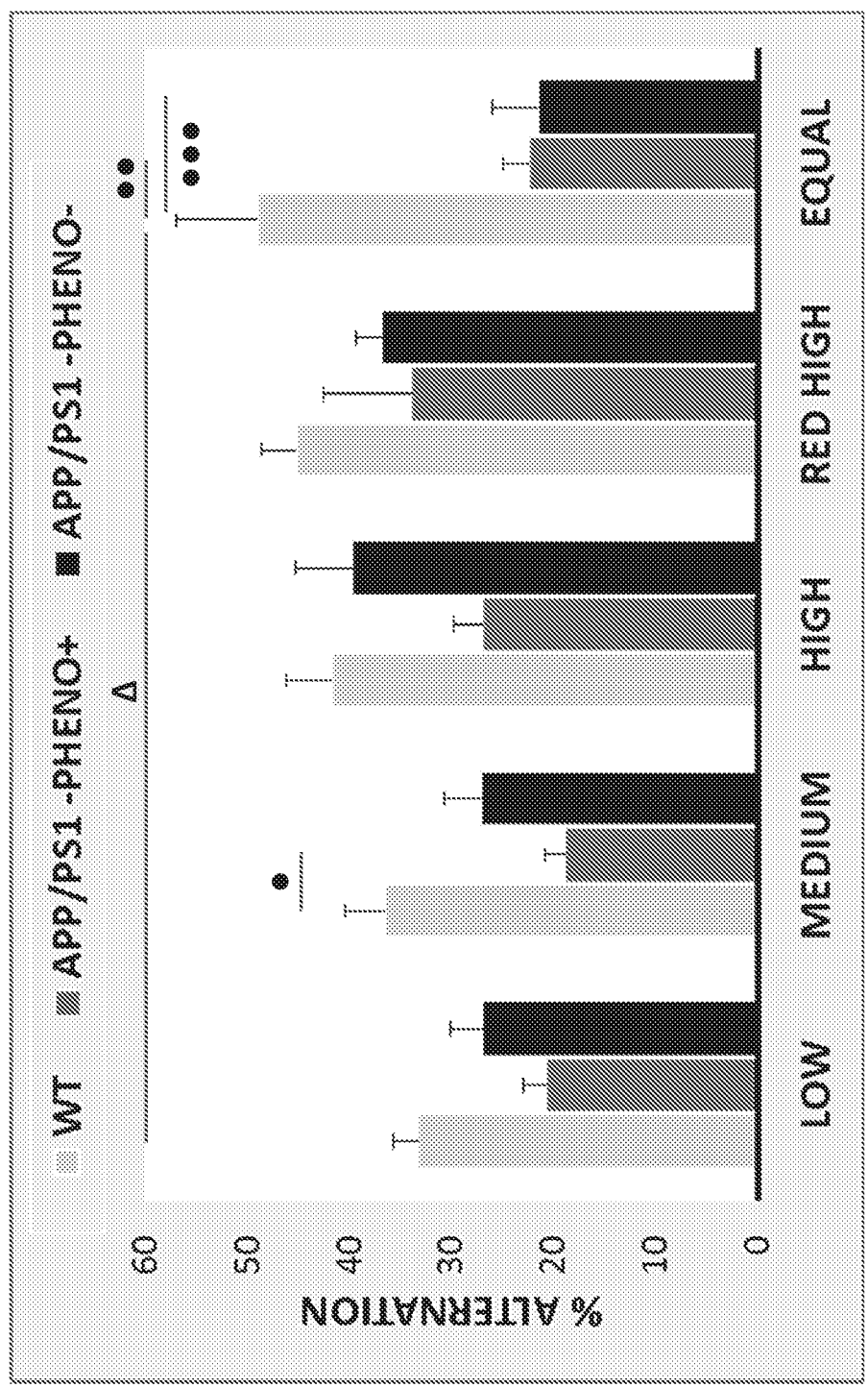
FIG. 14 depicts differences in percentage of alternation between wildtype and APP/PS1 transgenic mice in results of visual stimuli test that uses a maze of FIG. 11.

FIG. 14 depicts differences in percentage of alternation between wildtype and APP/PS1 transgenic mice in results of visual stimuli test that uses a maze of FIG. 11. Further detail of the alternation is described below:

Mixed Two-Way Repeated Measures ANOVA (One Factor Repetition)
Factor 1 (Groups) F=16.864 p<0.001
Factor 2 (Light Intensity) F=2.914 p=0.026
Factor 1×2 (Interaction) F=1.321 p=0.245
All Pairwise Multiple Comparison (Student-Newman-Keuls post-hoc test)
● Comparison between Groups (WT, PHENO+ and PHENO−) within Light Intensity.
Δ Comparison between Light Intensity (LOW, MEDIUM, HIGH, RED HIGH and EQUAL) within Groups.

Figure 15:
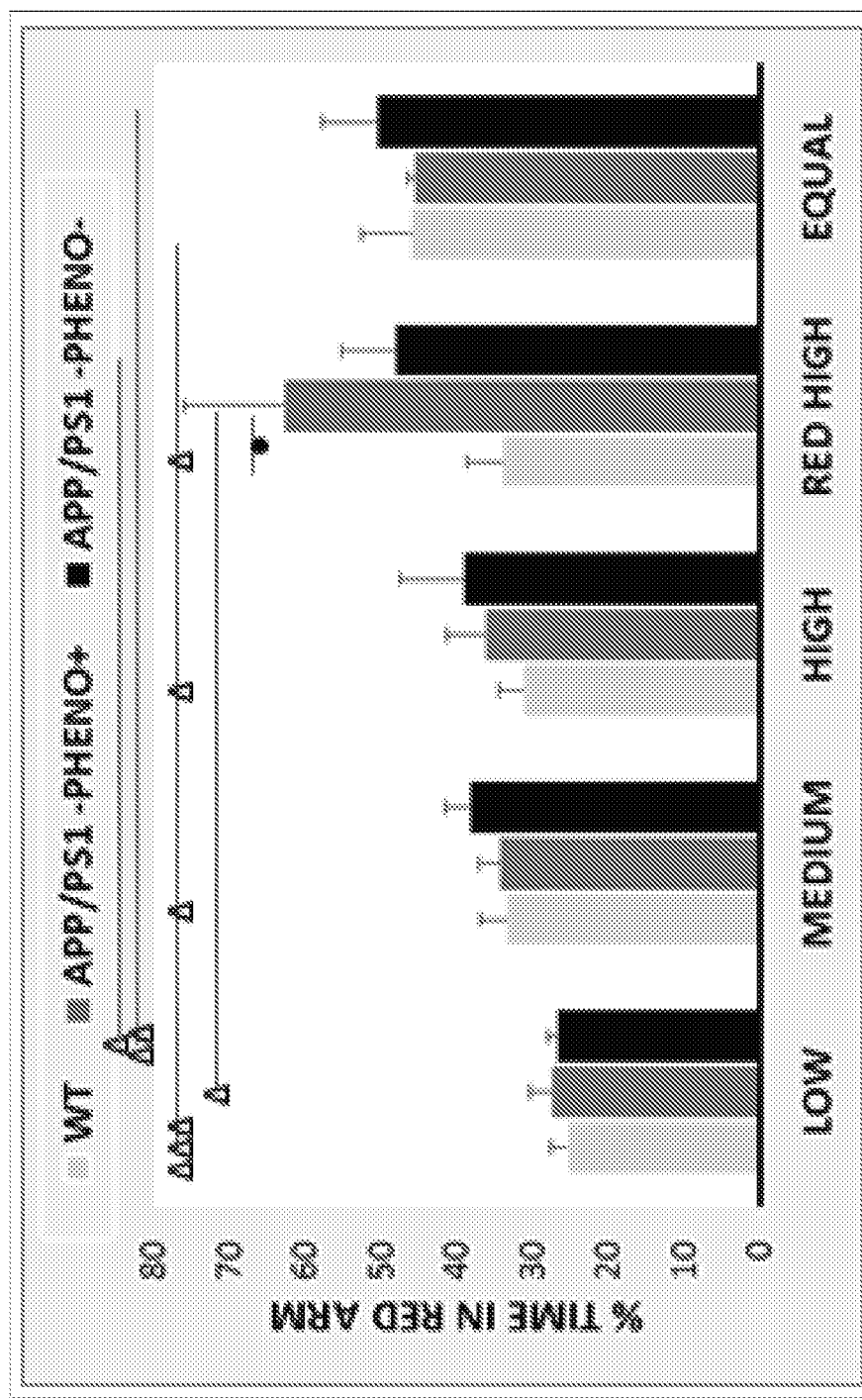
FIG. 15 depicts differences in percentage of time in red arm between wildtype and APP/PS1 transgenic mice in results of visual stimuli test that uses a maze of FIG. 11.

FIG. 15 depicts differences in percentage of time in red arm between wildtype and APP/PS1 transgenic mice in results of visual stimuli test that uses a maze of FIG. 11. Further detail of the alternation is described below:
Mixed Two-Way Repeated Measures ANOVA (One Factor Repetition)
Factor 1 (Groups) F=1.885 p=0.168
Factor 2 (Light Intensity) F=7.659 p<0.001
Factor 1×2 (Interaction) F=0.865 p=0.549
All Pairwise Multiple Comparison (Student-Newman-Keuls post-hoc test)
● Comparison between Groups (WT, PHENO+ and PHENO−) within Light Intensity.
Δ Comparison between Light Intensity (LOW, MEDIUM, HIGH, RED HIGH and EQUAL) within Groups.

Figure 16:
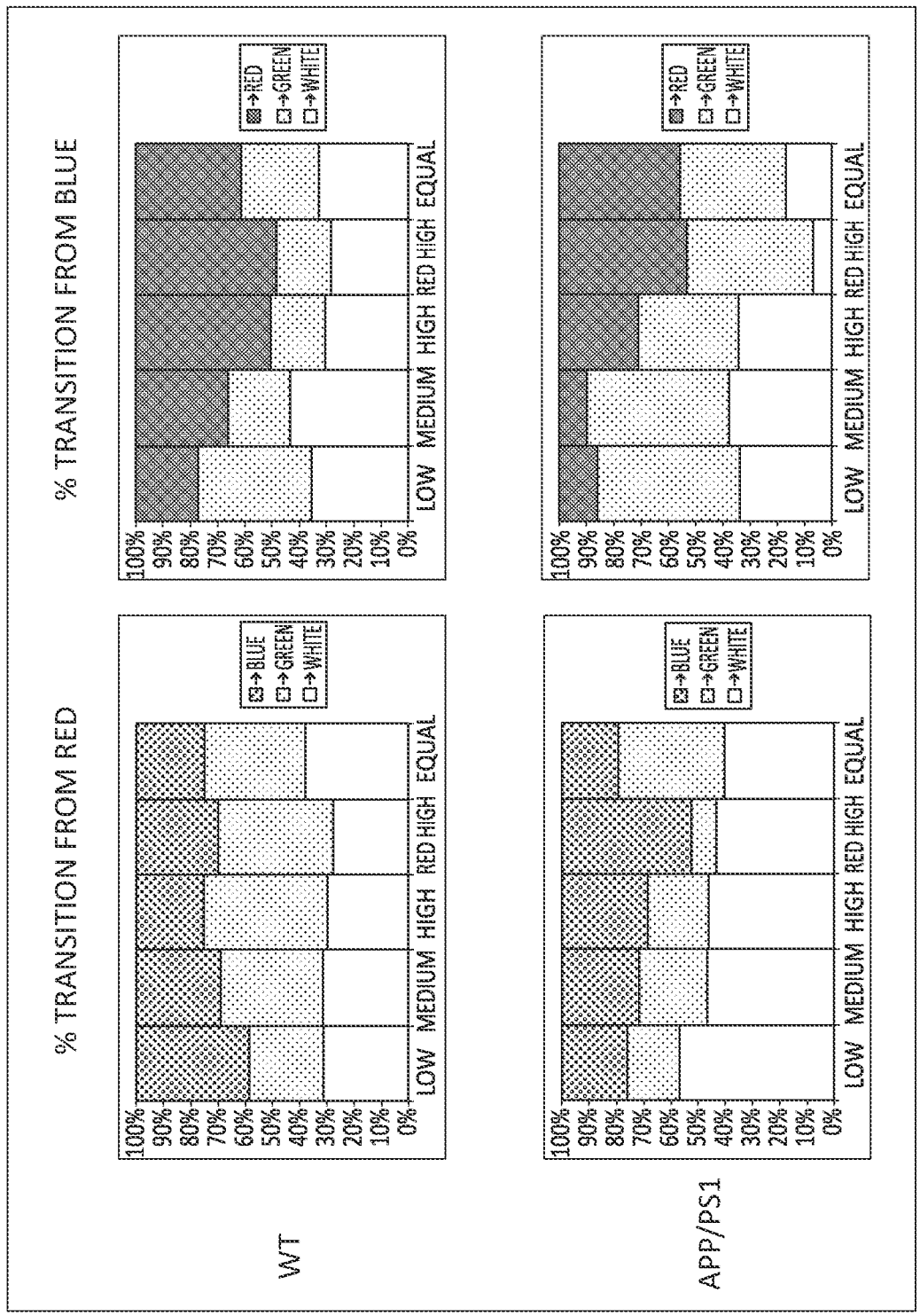
FIG. 16 depicts a percentage of percentage of transition from red and blue arms as a result of visual stimuli test that uses a maze of FIG. 11.
Figure 17:
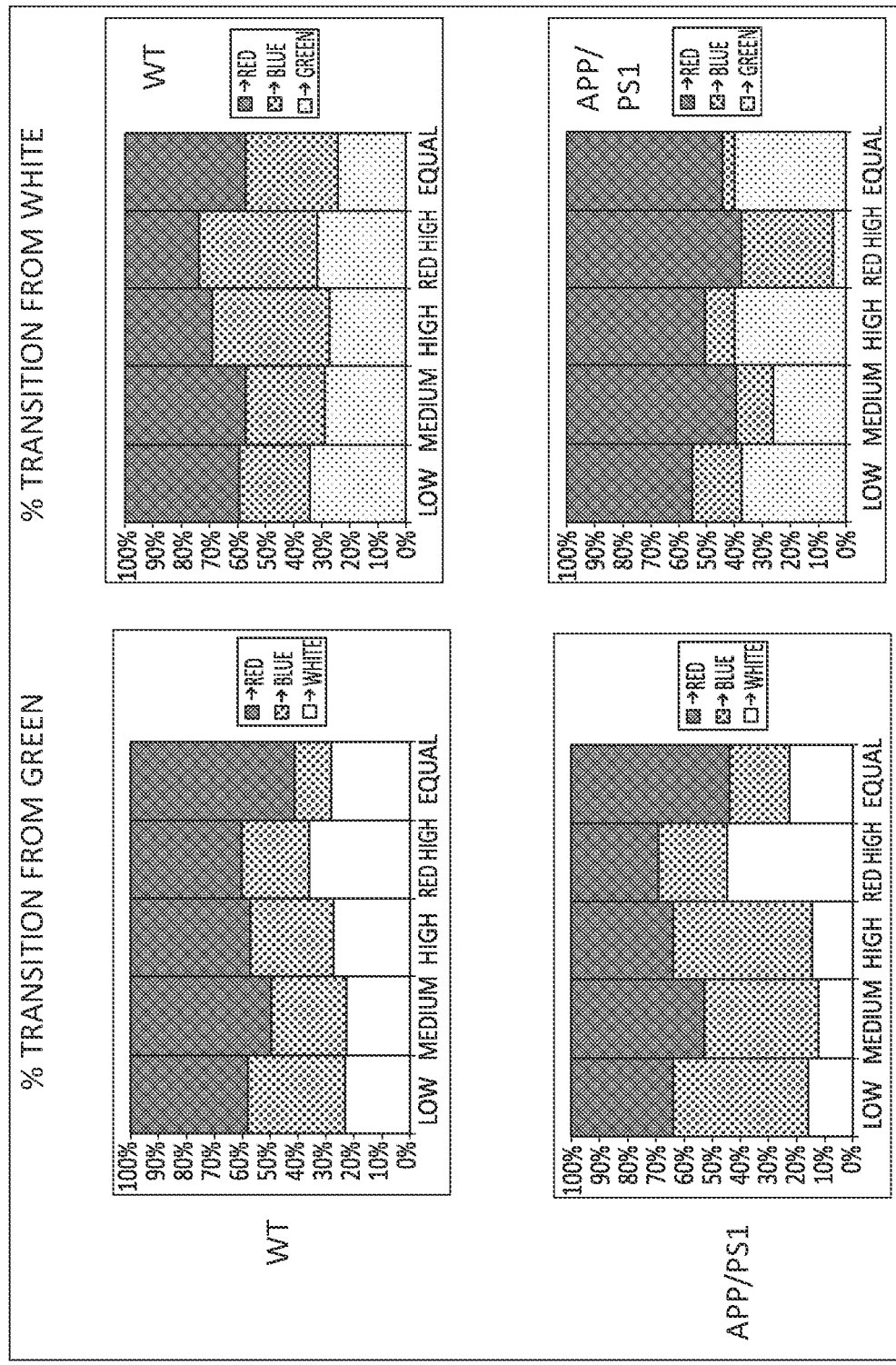
FIG. 17 depicts a percentage of percentage of transition from green and white arms as a result of visual stimuli test that uses a maze of FIG. 11.

FIG. 16 depicts a percentage of percentage of transition from red and blue arms as a result of visual stimuli test that uses a maze of FIG. 11. FIG. 17 depicts a percentage of percentage of transition from green and white arma as a result of visual stimuli test that uses a maze that is constructed in accordance with the principles of the present disclosure.

Figure 18:
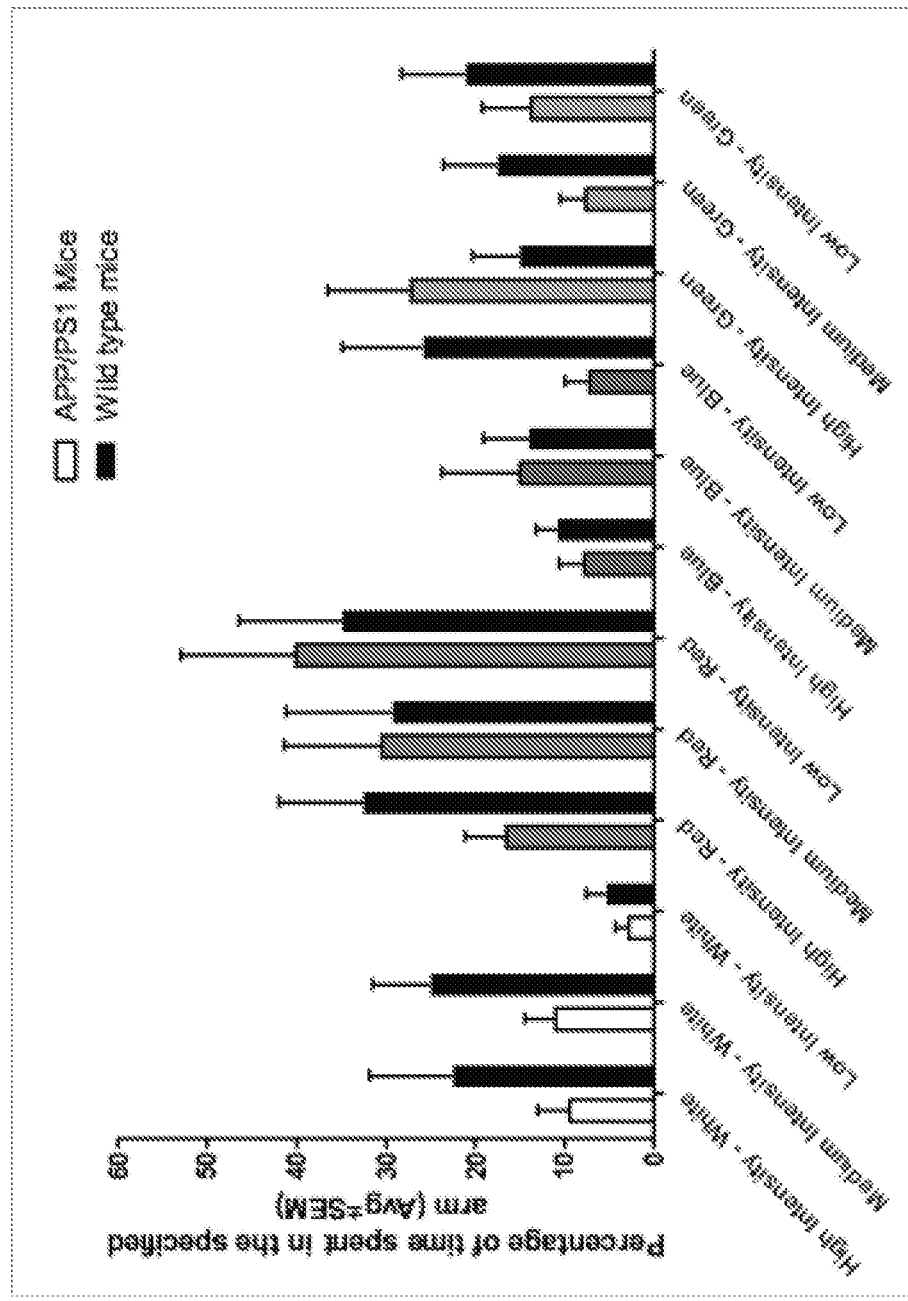
FIG. 18 depicts a chart showing a percentage of time spent in specified arm vs. the intensity of the colored arms.

FIG. 18 depicts a chart showing a percentage of time spent in specified arm vs. the intensity of the colored arms. FIG. 19 depicts a table showing a percentage that is displayed in FIG. 18.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A maze for evaluating a rodent, the maze comprising:
   a first room including a first visual marker;
   a second room including a second visual marker;
   a third room including a third visual marker; and
   a fourth room including a fourth visual marker;
   each of the first, second, third, and fourth rooms including side walls, a base floor, a floor plate, a cover positioned on the side walls, and an insertion gap between the floor plate and the base floor, the floor plate positioned above the base floor;
   wherein each of the first, second, third, and fourth visual markers is positioned in the respective insertion gap of the first, second, third, and fourth rooms;
   wherein the first, second, third, and fourth rooms are configured to allow the rodent to traverse between the rooms;
   wherein, in each of the first, second, third, and fourth rooms, the respective cover and the respective floor plates are configured to provide homogenized illumination by diffusing light from each of the first, second, third, and fourth visual markers respectively; and
   wherein each of the first visual marker, the second visual marker, the third visual marker, and the fourth visual marker is configured to illuminate, through the respective floor plate, an entirety of the first room, the second room, the third room, and the fourth room respectively.

2. The maze of claim 1, wherein the first visual marker, the second visual marker, the third visual marker, and the fourth visual marker are light sources emitting light at different wavelengths from one another.

3. The maze of claim 2, wherein each of the first visual marker, the second visual marker, the third visual marker, and the fourth visual marker comprises one or more light emitting diode (LED) strings.

4. The maze of claim 1, wherein the first, second, third, and fourth visual markers comprise at least four different hues of a color; and wherein any two of the first, second, third, and fourth visual markers have a contrast difference.

5. The maze of claim 1, wherein the first, second, third, and fourth visual markers are light sources emitting light in different colors.

6. The maze of claim 2, wherein the first visual marker emits light at a green light wavelength range, the second visual marker emits light at a red light wavelength range, the third visual marker emits light at a blue light range, and the fourth visual marker emits light at a white light wavelength range.

7. The maze of claim 2, further comprising a remote controller communicatively coupled to the light sources; and wherein respective intensities of light emitted from the light sources are adjustable through the remote controller.

8. The maze of claim 1, wherein the sidewalls are black; and wherein the floor plates and the covers are transparent.

9. The maze of claim 1, wherein the first room, the second room, the third room, and the fourth room extend from a central arena.

10. The maze of claim 9, wherein each of the first room, the second room, the third room, and the fourth room has a respective length greater than a central length of the central arena.

11. The maze of claim 1, wherein the first room, the second room, the third room, and the fourth room are configured such that upon entering any of the first, second, third, or fourth rooms, the rodent is fully immersed in respective illumination provided by the first, second, third, or fourth visual markers.

12. The maze of claim 1, wherein each of the first, second, third, and fourth rooms is positioned along a respective central axis that runs from a shared location in the central arena; and wherein each of the first, second, third, and fourth rooms extends outward at 90 degrees from two of the other rooms and 180 degrees from a third of the other rooms.

13. The maze of claim 8, wherein any two of the first, second, third, and fourth visual markers have a contrast difference.

14. A maze for evaluating a rodent, the maze comprising:
   a plurality of rooms, each of the plurality of rooms comprising a floor plate, a base floor, side walls, a removable cover on top of the side walls, and a set of light emitting diodes (LEDs), the set of LEDs positioned below the floor plate and within an LED insertion gap between the floor plate and the base floor;
   wherein the plurality of rooms are configured to allow the rodent to traverse between the rooms;
   wherein, in each of the plurality of rooms, the set of LEDs, the respective removable cover, and the respective floor plates are configured to provide homogenized illumination of an entirety of the respective arm; and
   wherein each set of LEDs errits light at different wavelength ranges.

15. A maze for evaluating a rodent, the maze comprising:
   a first room including a first visual marker;
   a second room including a second visual marker;
   a third room including a third visual marker; and
   a fourth room including a fourth visual marker;
   each of the first, second, third, and fourth rooms including side walls, a base floor, a floor plate, and an insertion gap between the floor plate and the base floor, the floor plate positioned above the base floor;
   wherein each of the first, second, third, and fourth visual markers is a set of LEDs;
   wherein each of the first, second, third, and fourth visual markers is positioned in the respective insertion gap of the first, second, third, and fourth rooms;

wherein the first, second, third, and fourth rooms are configured to allow the rodent to traverse between the rooms;

wherein in each room, each of the first visual marker, the second visual marker, the third visual marker, and the fourth visual marker is configured to illuminate the respective floor plate to provide a first contrast difference between the respective side walls and the respective floor plate; and wherein each of the first, second, third, and fourth visual markers are configured to have a second contrast difference with respect to any of the other three visual markers.

* * * * *